US008008350B2

(12) United States Patent
Luker et al.

(10) Patent No.: US 8,008,350 B2
(45) Date of Patent: Aug. 30, 2011

(54) BIPHENYLOXYACETIC ACID DERIVATIVES FOR THE TREATMENT OF RESPIRATORY DISEASE

(75) Inventors: Timothy Jon Luker, Loughborough (GB); Rukhsana Tasneem Mohammed, Loughborough (GB); Mark Dickinson, Loughborough (GB); Stephen Thom, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 6 days.

(21) Appl. No.: 12/089,276

(22) PCT Filed: Oct. 5, 2006

(86) PCT No.: PCT/GB2006/003697
§ 371 (c)(1),
(2), (4) Date: Apr. 4, 2008

(87) PCT Pub. No.: WO2007/039741
PCT Pub. Date: Apr. 12, 2007

(65) Prior Publication Data
US 2009/0036535 A1    Feb. 5, 2009

(30) Foreign Application Priority Data

| Oct. 6, 2005 | (GB) | 0520324.5 |
| Dec. 9, 2005 | (GB) | 0525082.4 |
| Feb. 11, 2006 | (GB) | 0602800.5 |

(51) Int. Cl.
C07C 317/22    (2006.01)
A61K 31/10    (2006.01)
(52) U.S. Cl. ......................... 514/571; 562/429
(58) Field of Classification Search ........................ None
See application file for complete search history.

(56) References Cited

U.S. PATENT DOCUMENTS

| 3,278,524 A | 10/1966 | Johnson et al. |
| 3,920,846 A | 11/1975 | Hanauye et al. |
| 3,985,779 A | 10/1976 | Tanaka et al. |
| 4,234,742 A | 11/1980 | Cognacq et al. |
| 4,248,618 A | 2/1981 | Serban et al. |
| 4,670,566 A | 6/1987 | Walsh et al. |
| 5,006,542 A | 4/1991 | Hall et al. |
| 5,145,790 A | 9/1992 | Mattingly et al. |
| 5,411,972 A | 5/1995 | Komoto et al. |
| 5,413,891 A | 5/1995 | Matsuura et al. |
| 5,532,371 A | 7/1996 | Komoto et al. |
| 5,703,099 A | 12/1997 | Hamanaka et al. |
| 6,150,413 A | 11/2000 | Bernardon et al. |
| 6,376,546 B1 | 4/2002 | Shoda et al. |
| 6,417,212 B1 | 7/2002 | Brooks et al. |
| 7,056,942 B2 | 6/2006 | Hildesheim et al. |
| 7,067,507 B2 | 6/2006 | Pulley et al. |
| 7,737,135 B2 | 6/2010 | Luker et al. |
| 2004/0029933 A1 | 2/2004 | Zhao et al. |
| 2004/0097555 A1 | 5/2004 | Ohkawa et al. |
| 2004/0220237 A1 | 11/2004 | Fu et al. |
| 2005/0239881 A1 | 10/2005 | Dunn et al. |
| 2006/0211765 A1* | 9/2006 | Pairaudeau et al. ........... 514/521 |
| 2006/0264435 A1* | 11/2006 | Bonnert et al. ........... 514/235.5 |
| 2006/0293352 A1 | 12/2006 | Bonnert et al. |
| 2007/0249686 A1 | 10/2007 | Bonnert et al. |
| 2008/0114002 A1 | 5/2008 | Bonnert et al. |
| 2008/0132480 A1 | 6/2008 | Luker et al. |
| 2008/0255150 A1 | 10/2008 | Luker |
| 2008/0293775 A1 | 11/2008 | Bonnert et al. |
| 2009/0012151 A1 | 1/2009 | Bonnert et al. |
| 2009/0036535 A1 | 2/2009 | Luker et al. |
| 2009/0149448 A1 | 6/2009 | Alcaraz et al. |
| 2009/0192163 A1 | 7/2009 | Luker et al. |
| 2010/0160285 A1* | 6/2010 | Luker et al. ............. 514/210.17 |

FOREIGN PATENT DOCUMENTS

| CH | 432119 | 9/1967 |
| EP | 0006789 | 1/1980 |
| EP | 0114734 | 8/1984 |
| EP | 0455058 | 11/1991 |
| EP | 0540165 | 5/1993 |
| EP | 0622690 | 11/1994 |
| EP | 0622816 | 11/1994 |
| EP | 0839808 | 5/1998 |
| EP | 1012142 | 6/2000 |
| EP | 1170594 | 1/2002 |
| EP | 1211513 | 6/2002 |
| EP | 1471057 | 10/2004 |
| GB | 690816 | 4/1953 |
| GB | 1 356 834 | 6/1974 |
| GB | 1 464 977 | 2/1977 |
| GB | 1 469 687 | 4/1977 |
| GB | 2 031 408 | 4/1980 |
| GB | 2 041 363 | 9/1980 |
| GB | 1 585 963 | 3/1981 |
| JP | 07140725 | 6/1995 |
| JP | 2003-508389 | 3/2003 |
| JP | 2006-521382 | 9/2006 |
| JP | 2006-522117 | 9/2006 |
| WO | WO 93/12086 | 6/1993 |
| WO | WO 97/08126 | 3/1997 |

(Continued)

OTHER PUBLICATIONS

Golub et al., Science, vol. 286, Oct. 15, 1999, pp. 531-537.*
Amin et al., "The Fries Reaction: Part VI—the rearrangement of aryl p-toluene-sulphonates & a convenient method for synthesis of hydroxy-diarylsulphones", *Journal of Scientific Industrial Research*, vol. 13B, 1954, pp. 181-183.
Atkinson et al., "Substituted (2-Phenoxyphenyl)acetic Acids with Antiinflammatory Activity", *J. Med. Chem.*, vol. 26, 1983, pp. 1353-1360.
Baliah et al., "Fries rearrangement of the benzenesulphonates of xylenols", *Recueil des Travaux Chimiques des Pays-Bas*, vol. 80, 1961, pp. 139-148.

(Continued)

Primary Examiner — Fiona T Powers
(74) Attorney, Agent, or Firm — Fish & Richardson P.C.

(57) ABSTRACT

The invention relates to substituted phenoxyacetic acids as useful pharmaceutical compounds for treating respiratory disorders, pharmaceutical compositions containing them, and processes for their preparation.

7 Claims, No Drawings

FOREIGN PATENT DOCUMENTS

| | | |
|---|---|---|
| WO | WO 98/03164 | 1/1998 |
| WO | WO 99/11605 | 3/1999 |
| WO | WO 99/11627 | 3/1999 |
| WO | WO 01/16120 | 3/2001 |
| WO | WO 01/60807 | 8/2001 |
| WO | WO 01/81312 | 11/2001 |
| WO | WO 01/92224 | 12/2001 |
| WO | WO 03/064387 | 8/2003 |
| WO | WO 03/066047 | 8/2003 |
| WO | WO 03/068744 | 8/2003 |
| WO | WO 03/097042 | 11/2003 |
| WO | WO 03/097598 | 11/2003 |
| WO | WO 03/101961 | 12/2003 |
| WO | WO 2004/007451 | 1/2004 |
| WO | WO 2004/048314 | 6/2004 |
| WO | WO 2004/058164 | 7/2004 |
| WO | WO 2004/089884 | 10/2004 |
| WO | WO 2004/089885 | 10/2004 |
| WO | WO 2004/094386 | 11/2004 |
| WO | WO 2004/096777 | 11/2004 |
| WO | WO 2005/018529 | 3/2005 |
| WO | WO 2005/044260 | 5/2005 |
| WO | WO 2005/105727 | 11/2005 |
| WO | WO 2005/115382 | 12/2005 |
| WO | WO 2006/005909 | 1/2006 |
| WO | WO 2006/021759 | 3/2006 |
| WO | WO 2006/037982 | 4/2006 |
| WO | WO 2006/056752 | 6/2006 |
| WO | WO 2006/125596 | 11/2006 |
| WO | WO 2007/039736 | 4/2007 |
| WO | WO 2007/039741 | 4/2007 |
| WO | WO 2007/052023 | 5/2007 |
| WO | WO 2007/068894 | 6/2007 |

OTHER PUBLICATIONS

Bartl et al., "Thioxanthene Derivatives of Pharmacological Interest: 1,2,4-Trichloro and 2,4,5,6- Tetrachloro Derivatives of 9-(3-Dimethylaminopropylidene)Thioxanthene", Collection Czechoslov. Chem. Commun., vol. 49, 1984, pp. 2295-2308.

Brown et al., "Some Chlorinated Hydroxyphenoxyacetic Acids", Journal of the Chemical Society, 1955, pp. 3681-3687.

Budavari, S., "The merck Index, 13$^{th}$ edition", p. 3106, monograph 3108, XP-002347170, 2001.

Cavill et al., "The chemistry of plant-growth regulators. Part I. 2:4-dichloro-6- hydroxyphenoxyacetic acid and related compounds", Journal of the Chemical Society, 1954, pp. 565-569.

Cecil Textbook of Medicine, 20$^{th}$ ed. (1996), vol. 2, pp. 1992-1996.
Cecil Textbook of Medicine, 20$^{th}$ ed. (1996), vol. 2, pp. 2050-2057.
Clemo et al., "Strychnine and brucine. Part II", Journal of the Chemical Society, vol. 125, 1924, pp. 1751-1804, XP008053173.

Cocco et al., "Annulation of functionalized hexadienones as an efficient regioselective approach to N-Aryl-2-(trifluoromethyl)-4-pyridinamines", Tetrahedron Letters, vol. 40, No. 23, 1999, pp. 4407-4410.

FDA mulls drug to slow late-stage Alzheimer's [online], [retrieved Sep. 24, 2003]. Retrieved from the Internet, URL; http://www.cnn.com/2003/HEALTH/conditions/09/24/alzheimers.drug.ap/index.html>.

Gallo et al., "Spirodioxolanonarenones. II. Synthesis of a halogenated 1,4-dioxaspiro[4,5]deca-7,9- diene-2,6-dione", Journal of Chemistry, vol. 30, No. 5, 1965, pp. 1657-1658.

Gaunt et al., "Metabolism of 4-chloro-2-methylphenoxyacetate by a soil pseudomonad", Biochem. J., vol. 122, 1971, pp. 519-526.

Hazeldine et al., "Design, Synthesis and Biological Evaluation of Analogues of the Antitumor Agent, 2- {4-[(7-Chloro-2-quinoxalinyl)oxy]phenoxyl }propionic Acid (XK469)", J. Med. Chem., vol. 44, 2001, pp. 1758-1776.

Huston et al., "Chloro derivatives of o- and p-benzyl phenols. II. Some monochloro, dichloro and trichloro derivatives of ortho and para benzyl phenols", Journal of the American Chemical Society, vol. 55, No. 11, 1933, pp. 4639-4643.

Inukai et al., "ortho-Disubstituted F-benzenes. III. Preparation of (F-benzo)heterocyclic compounds from F-benzoic acid and F-phenol, and the reactions of some intermediary F-benzoyl- and F-phenoxy compounds", Bull. Chem. Soc. Jpn., vol. 54, No. 11, 1981, pp. 3447-3452.

Janczewski et al., "Effect of Molecular Structure on Optical Properties of Sulfoxide Systems. o-Phenoxyphenylsulfinylacetic Acid and some of Their Derivatives. Part II", Polish Journal of Chemistry, vol. 62, No. 1-3, 1964, pp. 91-105, XP008053171.

Kmonicek et al., "(Tert-Amino)-11-(4-Methylpiperazino)Dibenzo[b,f]Thiepins and their 10,11- Dihydro Derivatives; Synthesis and Neuroleptic Activity", Collection Czechoslov. Chem. Commun., vol. 52, 1987, pp. 792-803, XP-002347166.

Lehmler et al., "Synthesis of hydroxylated PCB metabolites with the Suzuki-coupling", Chemosphere, vol. 45, 2001, pp. 1119-1127.

Litvak et al., "Synthesis and $S_NAr$ reactions of new dioxins and predioxins", Chemosphere, vol. 43, No. 4-7, 2001, pp. 493-495.

Lupus erythematosus[online], [retrieved Dec. 28, 2006]. Retrieved from the Internet, URL; http://en.wikipedia.org/wiki/Lupus_erythematosus>.

Maeda et al., "Studies on the Synthesis and Analgesic and Anti-inflammatory Activities of 2-Thiazolylamino- and 2-Thiazolyloxy-arylacetic Acid Derivatives", Chem. Pharm. Bull., vol. 31, No. 10, 1983, pp. 3424-3445, XP-002347167.

Manoury et al., "Synthesis and Analgesic Activities of Some (4-Substituted phenyl-1- piperazinylalkyl 2-Aminobenzoates and 2-Aminonicotinates", Journal of Medicinal Chemistry, vol. 22(5), pp. 554-559 (1979).

Meunier et al., "Photochemical behaviour of dichlorprop [(±)-2-(2,4-dichlorophenoxy)propanoic acid] in aqueous solution", Pest Management Science, vol. 58, No. 8, 2002, pp. 845-852.

Moser et al., "Synthesis and Quantitative Structure-Activity Relationships of Diclofenac Analogues", J. Med. Chem., vol. 33, 1990, pp. 2358-2368 , XP-001024801.

Moshchitskii et al., "Smiles rearrangement of tetrachloropyridyl methyl-hydroxyphenyl sulfone", Chemistry of Heterocyclic Compounds, vol. 15, No. 7, 1979, pp. 1085-1088.

Ong et al., "Synthesis and Analgesic Activity of Some Spiro[dibenz[b,f]oxepin-10,4'-piperidine] Derivatives", J Med. Chem., vol. 22, No. 7,1979, pp. 834-839, XP-002347163.

Rajsner et al., "Fluorinated tricyclic Neuroleptics: Synthesis and Pharmacology of 8-Fluoro-4-(4- Methylpiperazino)-4,5-Dihydrothieno[2,3-b]-1-Benzothiepin", Collection Czechoslov. Chem. Commun., vol. 44, 1979, pp. 2997-3007, XP-002347164.

Selvi et al., "Vilsmeier cyclization of 2-amino phenoxyacetic acid", Synthetic Communications, vol. 31, No. 14, 2001, pp. 2199-2202.

Sindelar et al., "Synthesis of 3-Chloro-5-(4-Methylpiperazino)-6,7-Dihydro-5H-Dibenzo[b,g]Thiocin, An Eight-Membered Ring Homologue of The Neuroleptic Agent Octoclothepin", Collection Czechoslov. Chem. Commun., vol. 45, 1980, pp. 491-503, XP-002347160.

Sindelar et al., "Fluorinated Tricyclic Neuroleptics with Prolonged Action: 3-Fluoro-8-Trifluoromethyl Derivatives of 10-(4-Methylpiperazino)- and 10[4-(2-Hydroxyethyl)Piperazino]- 10,11-Dihydrodibenzo-[b,f]Thiepin", Collection Czechoslov. Chem. Cornmun., vol. 46, 1981, pp. 118-140, XP-002347168.

Sindler-Kulyk et al., "Synthesis of New 3-(Phenoxyphenyl)sydnones", J. Hetercyclic Chem., vol. 29, No. 2, 1992, pp. 1013-1015, XP-002347161.

Stokker et al., "3-Hydroxy-3-methylglutaryl-coenzyme A Reductase Inhibitors. 5. 6-(Fluoren-9-yl)- and 6-(Fluoren-9-ylidenyl)-3,5-dihydroxyhexanoic Acids and Their Lactone Derivatives", J. Med. Chem. 29:852-855 (1986).

Thuillier, G., "Derives des acides 24 aryloxyacetiques a activite neurotrope", Chimique Therapeutique, vol. 1, No. 2, 1966, pp. 82-86.

Walsh et al., "Antiinflammatory Activity of N-(2-Benzoylphenyl)alanine Derivatives", J. Med. Chem., vol. 27, 1984, pp. 1317-1321, XP-002347162.

Wheatley et al., "2-Benzylphenol Derivatives. III. Basic Ethers", Journal of American Chemical Society, vol. 71, No. 11, 1949, pp. 3795-3797.

Database CA [Online] Chemical Abstracts Service, Columbus, Ohio, US; XP002372494 retrieved from STN Database accession No. 1956:16264 abstract & Ott, Donald G. et al: "A carbon-14 tracer study of the alkaline rearrangement of chlorophenanthraquinones" Journal of the American Chemical Society, 77, 2325-9 CODEN:JACSAT; ISSN:0002-7863, 1955.

Database Caplus [Online] Chemical Abstracts Service, Columbus, Ohio, US; 1992, XP002372495 retrieved from STN Database accession No. 1992:255529 abstract & Ram, Bhagat et al: "Potential hypolipidemic agents part VI: synthesis and biological activity of some new 4-chloro/methyl-2-pyrazolylphenoxy alkanoates" Indian Drugs, vol. 29, No. 6, 1992, pp. 258-262.

Database WPI 1-3, 5, Section Ch, Week 200365 19, 20, Derwent Publications Ltd., London, GB, AN 2003-689635 XP-002301315, WO03068744A1, Ishihara Sangyo Kaisha, Ltd., Aug. 21, 2003.

STN International, File Caplus, Caplus accession 1-10, No. 1987:597776, document No. 107:197776, Otsuka Pharmaceutical Factory, "Preparation of aminophenol derivatives as anticoagulants, analgesics, hypotensives, and diuretics", JP, A2, 62108859, 19870520.

STN International, File Caplus, Caplus accession 1-5, 10, No. 1979:186607, document No. 90:186607, Ciba-Geigy, "Phenoxyphenoxyalkanecardoxylic acid derivatives", DE, A1, 2832435, 19790208.

STN International, File Caplus, Caplus accession 1-5, 10, No. 1971:53748, document No. 74:53748, Walker et al., "Synthesis of 5-phenyl-2,3,4,5-tetrahydro-1,4-benzoxazepines and corresponding 3-ones", & *Journal of Organic Chemistry* (1970), 36(2), 305-308.

STN International, File Caplus, Caplus accession 1-3, 5, 10, No. 1992:407796, document No. 117:7796, Tokuyama Soda Co., Ltd., "Preparation of thienyloxphenoxy group-containing carboxylic acids as microbicides", JP, A2, 04021677, 19920124.

STN International, File Caplus, Caplus accession 1-3, 5, 10, No. 1975:402045, document No. 83:2045, Shiley et al., "Fungicidal activity of some fluoroaromatic compounds", *Journal of Fluorine Chemistry* (1975), 5(4), 371-376.

STN International, File Caplus, Caplus accession 1, 3, 5, 10, No. 1972:405106, document No. 77:5106, Oniscu et al., "Monoethanolaminosulfonyl-,diethanolaminosulfonyl- and morpholinosulfonyl-phenoxyacetic derivatives", Buletinul Institutului Politehnic din Iasi, (1971), 14(3-4), 101-114.

STN International, File Caplus, Caplus accession 1, 3, 5, 10, No. 1961:22702, document No. 55:22702, Takano, K., "Condensation products of furfuryl alcohol. IV. Condensation products of furfuryl alcohol with cresols", Nippon Kagaku Zasshi (1959), 80, 678-681.

STN International, File Caplus, Caplus accession 1, 3-5, 10, No. 1958:25331, document No. 52:25331, Landa et al., "Properties of sulfide catalysts. V. Preparation of alkylphenols", Chemicke Listy pro Vedu a Prumysl (1957), 51, 1851-1857.

STN Intenational, File Caplus, Caplus accession 1, 3, 5, 10, No. 1971:498288, document No. 75:98288, Botez et al., "Phenoxybutyric acid sulfamides. I. Sulfamide derivatives of the α-phenoxy-, α-cresoxy-, and α-xylenoxybutyric acids", Buletinul Institutului Politehnic din Iasi (1970), 16(1-2), 161-172.

Vippagunta etal., "Crystalline solids", *Advanced Drug Delivery Reviews* 48:3-26 (2001).

Inflammatory Bowel Disease [online] {retrieved on Apr. 7, 2008 from the internet} {URL:http://vvvvw.emedicinehealth.com/script/main/art.asp?articlekey=59121&pf=3&page=8}.

Rheumatoid arthritis [online] {retrieved on Apr. 7, 2008 from internet} {URL:http://www.nlm.nih.gov/medlineplus/ency/article/000431.htm}.

Asthma [online] [retrieved on May 30, 2008] retrieved from the Internet URL:http://www.nlm.nih.gov/medlineplus/ency/article/000141.htm.

Chiu et al., "Derivation and Properties of Recombinant Fab Antibodies to Coplanar Polychlorinated Biphenyls", *J. Agric. Food Chem.* 48:2614-2624 (2000).

Morissette et al., "High-throughput crystallization: polymorphs, salts, co-crystals and solvates of pharmaceutical solids", *Advanced Drug Delivery Reviews* 56:275-300 (2004).

Rhinitis [online] retrieved on Nov. 12, 2008. Retrieved from URL; http://www.healthline.com/galecontent/rhinitis?print=true.

RN 110624-55-0, retrieved from Caplus; retrieved on Apr. 7, 2008.

USPTO Office Action in U.S. Appl. No. 10/552,082, mailed Oct. 29, 2007, 6 pages.

Fish & Richardson P.C., Amendment in Reply to Action of Oct. 29, 2007 in U.S. Appl. No. 10/552,082, filed Feb. 29, 2008, 18 pages.

USPTO Final Office Action in U.S. Appl. No. 10/552,082, mailed Jun. 9, 2008, 18 pages.

Fish & Richardson P.C., Amendment in Reply to Action of Jun. 9, 2008 in U.S. Appl. No. 10/552,082, filed Sep. 9, 2008, 11 pages.

USPTO Office Action in U.S. Appl. No. 10/552,082, mailed Dec. 4, 2008, 23 pages.

Fish & Richardson P.C., Amendment in Reply to Action of Dec. 4, 2008 in U.S. Appl. No. 10/552,082, filed Apr. 6, 2009, 8 pages.

USPTO Notice of Allowance in U.S. Appl. No. 10/552,082, mailed Jul. 1, 2009, 9 pages.

USPTO Office Action in U.S. Appl. No. 10/569,065, mailed May 4, 2007, 12 pages.

Fish & Richardson P.C., Amendment in Reply to Action of May 4, 2007 in U.S. Appl. No. 10/569,065, filed Aug. 3, 2007, 14 pages.

USPTO Final Office Action in U.S. Appl. No. 10/569,065, mailed Oct. 17, 2007, 4 pages.

Fish & Richardson P.C., Amendment in Reply to Action of Oct. 17, 2007 in U.S. Appl. No. 10/569,065, filed Jan. 17, 2008, 9 pages.

USPTO Office Action in U.S. Appl. No. 10/569,065, mailed Apr. 16, 2008, 14 pages.

Fish & Richardson P.C., Amendment in Reply to Action of Apr. 16, 2008 in U.S. Appl. No. 10/569,065, filed Jul. 16, 2008, 38 pages.

USPTO Office Action in U.S. Appl. No. 10/569,065, mailed Oct. 28, 2008, 15 pages.

Fish & Richardson P.C., Amendment in Reply to Action of Oct. 28, 2008 in U.S. Appl. No. 10/569,065, filed Jan. 27, 2009, 7 pages.

USPTO Office Action in U.S. Appl. No. 10/569,065, mailed May 13, 2009, 10 pages.

Fish & Richardson P.C., Amendment in Reply to Action of May 13, 2009 in U.S. Appl. No. 10/569,065, filed Jul. 14, 2009, 9 pages.

USPTO Office Action in U.S. Appl. No. 11/574,076, mailed Oct. 27, 2008, 23 pages.

Fish & Richardson P.C., Amendment in Reply to Action of Oct. 27, 2008 in U.S. Appl. No. 11/574,076, filed Apr. 27, 2009, 21 pages.

USPTO Office Action in U.S. Appl. No. 11/574,076, mailed Aug. 18, 2009, 7 pages.

USPTO Office Action in U.S. Appl. No. 11/576,372, mailed Jul. 22, 2009, 19 pages.

USPTO Office Action in U.S. Appl. No. 12/092,431, mailed Aug. 4, 2009, 8 pages.

Atkinson et al., "Substituted (2-Phenoxyphenyl)acetic Acids with Antiinflammatory Activity", *J. Med. Chem.*, vol. 26, 1983, pp. 1353-1360.

Dalal et al., "Synthetic insecticides. I. Synthesis of a, a-bis(aryl)-β, β, γ-trichlorobutanes", STN Accession No. 1950:35789, Document No. 44:35789, Abstract of Journal of the Indian Chemical Society 26:549-52 (1949).

Gavezzotti, "Are Crystal Structures Predictable?", *Acc. Chem. Res.* 27:309-314 (1994).

Hazlet et al., "Bromination of 2-phenylphenyl acetate", STN Accession No. 1941:37645, Document No. 35:37645, Abstract of Journal of the American Chemical Society 63:1890-2 (1941).

Ly et al., "Small-molecule CRTH2 antagonists for the treatment of allergic inflammation: an overview", *Expert Opin. Invest. Drugs* 14(7):769-773 (2005).

Manske et al., "Synthesis and Reactions of Some Dibenzoxepins", *Journal of American Chemical Society* 72:4797-4799 (1950).

Ueda et al., "The Synthesis of 10-(4-Methylpiperazino)dibenzo[bf] thiepin and Related Compounds. Neurotropic and Psychotropic Agents", *Chem. Pharm. Bull.* 23(10):2223-2231 (1975).

Ulven et al., "Targeting of the Prostaglandin $D_2$ Receptors Dp and CRTH2 for Treatment of Inflammation", *Current Topics in Medicinal Chemistry* 6:1427-1444 (2006).

Fish & Richardson P.C., RCE and Interview Summary in response to Notice of Allowance of Jul. 1, 2009 in App. U.S. Appl. No. 10/552,082, filed Sep. 30, 2009, 2 pages.

USPTO Office Action in U.S. Appl. No. 10/552,082, mailed Jan. 7, 2010, 12 pages.

USPTO Office Action in U.S. Appl. No. 10/551,783, mailed Dec. 7, 2009, 15 pages.

Fish & Richardson P.C., Amendment in Reply to Action of Dec. 7, 2009 in U.S. Appl. No. 10/551,783, filed Mar. 8, 2010, 17 pages.
USPTO Notice of Allowance in U.S. Appl. No. 10/569,065, mailed Oct. 23, 2009, 10 pages.
Fish & Richardson P.C., RCE and IDS in Reply to Notice of Allowance of Oct. 23, 2009 in U.S. Appl. No. 10/569,065, filed Nov. 5, 2009, 3 pages.
USPTO Notice of Allowance in U.S. Appl. No. 10/569,065, mailed Jan. 28, 2010, 9 pages.
USPTO Office Action in U.S. Appl. No. 11/571,707, mailed Mar. 12, 2010, 16 pages.
Fish & Richardson P.C., RCE and Amendment in Reply to Action of Aug. 18, 2009 in U.S. Appl. No. 11/574,076, filed Dec. 18, 2009, 13 pages.
USPTO Notice of Allowance in U.S. Appl. No. 11/574,076, mailed Feb. 3, 2010, 12 pages.
Fish & Richardson P.C., Amendment in Reply to Action of Jul. 22, 2009 in U.S. Appl. No. 11/576,372, filed Jan. 22, 2010, 18 pages.
Fish & Richardson P.C., Amendment in Reply to Action of Aug. 4, 2009 in U.S. Appl. No. 12/092,431, filed Feb. 3, 2010, 15 pages.
USPTO Office Action in U.S. Appl. No. 12/167,513, mailed Nov. 2, 2009, 19 pages.
Fish & Richardson P.C., Amendment in Reply to Action of Nov. 2, 2009 in U.S. Appl. No. 12/167,513, filed Feb. 2, 2010, 19 pages.
AstraZeneca AB: WO03066046 & WO03066047, "The use of indole-3-acetic acids as CRTH2 receptor antagonists", *Expert Opin. Ther. Patents* 14(1):125-128 (2004).
Ebenezar et al., "Prostaglandins in the patent literature", *Expert Opin. Ther. Patents* 17(9):1131- 1145 (2007).
Ono Pharm. Co. Ltd: WO03022813 & WO03022814, "The use of prostaglandin D2 receptor antagonists to treat allergic rhinitis", *Expert Opin. Ther. Patents* 13(10):1657-1661 (2003).
Wermuth, "Molecular Variations Based on Isosteric Replacements", the Practice of Medicinal Chemistry, 1996, chapter 13, pp. 203-237.
Preventing Asthma Symptoms [online] [retrieved on Apr. 23, 2010 from the interne] URL:http://www.webmd.com/asthma/guide/astluna-prevention.
Allergic Rhinitis—Prevention [online] [retrieved on Apr. 23, 2010 from the internet] URL:http://www.webmd.com/allergies/tc/allergic-rhinitis-prevention.
COPD Treatments: Improving Your Quality of Life [online] [retrieved on Apr. 23, 2010 from the interne] URL:http://www.webmd.com/lung/copd/copd-treatments-improving-your-quality-of-life.
Fish & Richardson P.C., Amendment in Reply to Action of Jan. 7, 2010 in U.S. App. U.S. Appl. No. 10/552,082, filed Jul. 2, 2010, 8 pages.
USPTO Office Action in U.S. App. U.S. Appl. No. 10/551,783, mailed Apr. 23, 2010, 9 pages.
Fish & Richardson P.C., RCE and IDS in Reply to Notice of Allowance of Jan. 28, 2010 in U.S. Appl. No. 10/569,065, filed Mar. 31, 2010, 5 pages.
USPTO Notice of Allowance in U.S. Appl. No. 10/569,065, mailed May 13, 2010, 10 pages.
USPTO Final Office Action in U.S. Appl. No. 11/576,372, mailed May 7, 2010, 7 pages.
USPTO Office Action in U.S. Appl. No. 11/719,832, mailed Apr. 30, 2010, 20 pages.
USPTO Final Office Action in U.S. Appl. No. 12/092,431, mailed May 4, 2010, 13 pages.
USPTO Final Office Action in U.S. Appl. No. 12/167,513, mailed Apr. 22, 2010, 22 pages.
STN International, File Caplus, Caplus accession 1-7, 10, No, 1986:109631, document No, 104:109631,Yoshitorni Pharmaceutical Industries, Ltd., "Imidazole derivatives", JP, A2, 60142965, 19850729.
Vippagunta et al., "Crystalline solids", *Advanced Drug Delivery Reviews* 48:3-26 (2001).
Inflammatory Bowel Disease [online] {retrieved on Apr. 7, 2008 from the internet} {URL:http://www.emedicinehealth.com/script/main/art. asp?articlekey-59121&pf=3&p.=8).
AZZZ2 Rheumatoid arthritis [online] {retrieved on Apr. 7, 2008 from the Internet} URL: http://www.nlm.nih.gov/medlineplus/ency/article/000431.htm{.
Asthma [online] [retrieved on May 30, 2008] retrieved from the Internet URL:http://www.nlm.nih.gov/medlineplus/ency/article/000141.htm.
Berhenke et al., "Some Aryloxyaliphatic Acids", *Journal of the American Chemical Society* 73:4458 (1951).
Chemical abstract 123:213132 in CAS (or JP07140725) , 1995.
Chemical abstract 123:22081 in CAS (or EP622690) , 1995.
Chemical abstract 116:123167 in CAS (or EP455058) , 1992.
Chemical abstract 85:56485 in CAS or Parli et al., "The relation between the metabolism of 2,4dichloro-6-phenylphenoxyethylamine (DPEA) and related compounds and their activities as microsomal mono-oxygenase inhibitors", Drug Metabolism and Disposition 1(4):628-33 (1973).
Chemical abstract 69:93942 in CAS or Cheng et al., "Phenylphenol derivatives with biological activity. III. Fungistatic activity of phenylphenol derivatives", Agricultural and Biological Chemistry 32(9):1162-74 (1968).
Chemical abstract 49:86470 in CAS or Mel'nikov et al., "Structure and physiological activity of alkyl- and aryl-phenoxyacetic acids and their derivatives", Fiziologiya Rastenii 2:267-70 (1955).
Chemical abstract 35:37645 in CAS or Hazlet et al., "The Bromination of 2-Phenylphenyl Acetate", Journal of the American Chemical Society 63:1890-2 (1941).
Coxworth, "Synthesis of Chlorinated 2-(3-Benzofuranyl)Phenols", *Canadian Journal of Chemistry* 44:1092-1096 (1966).
"DialogWeb Records", http://www.dialogweb.com/cgi/document?req=1284661379410, accessed 16 Sep. 2010.
Fromageot et al., "Photodecarboxylation of 2-(2'-carboxymethoxy-5'-methylphenyl)-benzotriazole", *Journal of Photochemistry and Photobiology, A: Chemistry* 44(1):93-98 (1988).
Hazlet et al., "The Bromination of 2-Phenylphenyl Acetate", *Journal of the American Chemical Society* 63:1890-2 (1941).
Ram et al., "Potential Hypolipidemic Agents Part VI: Synthesis and Biological Activity of Some New 4-Chloro/Methyl-2-pyrazolylphenoxy Alkanoates", *Indian Drugs* 29(6), 258-262 (1992).
Database Beilstein chemical extract accession No. 6722243, Jan. 2010 .
Database Beilstein chemical extract accession No. 6722682, Jan. 2010 .
Database Beilstein chemical extract accession No. 3532059, Jan. 2010 .
Database Beilstein chemical extract accession No. 2533336, Jan. 2010 .
Database Beilstein chemical extract accession No. 2537173, Jan. 2010.
Database Beilstein chemical extract accession No. 3385275, Jan. 2010.
Database Beilstein chemical extract accession No. 3386554, Jan. 2010.
USPTO Notice of Allowance in U.S. Appl. No. 10/552,082, mailed Sep. 15, 2010, 12 pages.
Fish & Richardson P.C., Amendment in Reply to Action of Apr. 23, 2010 in App. U.S. Appl. No. 10/551,783, filed Jul. 2, 2010, 23 pages.
USPTO Office Action in U.S. Appl. No. 10/551,783, mailed Sep. 7, 2010, 6 pages.
Fish & Richardson P.C., RCE and IDS in reply to Notice of Allowance of Sep. 7, 2010 in U.S. Appl. No. 10/551,783, filed Dec. 6, 2010, 4 pages.
Fish & Richardson P.C., RCE and IDS in Reply to Notice of Allowance of May 13, 2010 in U.S. Appl. No. 10/569,065, filed Aug. 2, 2010, 4 pages.
USPTO Notice of Allowance in U.S. Appl. No. 10/569,065, mailed Sep. 1, 2010, 9 pages.
Fish & Richardson P.C., RCE and IDS in Reply to Notice of Allowance of Sep. 1, 2010 in U.S. Appl. No. 10/569,065, filed Nov. 8, 2010, 5 pages.

USPTO Notice of Allowance in U.S. Appl. No. 10/569,065, mailed Dec. 2, 2010, 10 pages.
Fish & Richardson P.C., Amendment in Reply to Action of Mar. 12, 2010 in U.S. Appl. No. 11/571,707, mailed Nov. 22, 2010, 12 pages.
USPTO Notice of Allowance in U.S. Appl. No. 11/571,707, mailed Nov. 22, 2010, 12 pages.
Fish & Richardson P.C., Response to Notice of Allowance of Feb. 3, 2010 in U.S. Appl. No. 11/574,076, filed Apr. 30, 2010, 2 pages.
Fish & Richardson P.C., Reply to Action of May 7, 2010 in U.S. Appl. No. 11/576,372, filed Aug. 9, 2010, 10 pages.
USPTO Office Action in U.S. Appl. No. 11/576,372, mailed Sep. 2, 2010, 7 pages.
Fish & Richardson P.C., RCE, IDS and Amendment in Reply to Action of Sep. 2, 2010 in U.S. Appl. No. 11/576,372, filed Dec. 2, 2010, 16 pages.
Fish & Richardson P.C., Amendment in Reply to Action of Apr. 30, 2010 in U.S. Appl. No. 11/719,832, filed Aug. 30, 2010, 18 pages.
USPTO Office Action in U.S. Appl. No. 11/719,832, mailed Oct. 6, 2010, 12 pages.
Fish & Richardson P.C., RCE, IDS and Amendment in Reply to Action of May 4, 2010 in U.S. Appl. No. 12/092,431, filed Sep. 7, 2010, 16 pages.
Fish & Richardson P.C., RCE, IDS and Amendment in Reply to Action of Apr. 22, 2010 in U.S. Appl. No. 12/167,513, filed Oct. 22, 2010, 22 pages.
Burger, "Isosterism and bioisosterism in drug design", in Progress in Drug Research 287-328 (Ernst Jucker, ed., Birkhauser Verlag, 1991).
Patani et al., "Bioisosterism: a Rational Approach in Drug Design", *Chem. Rev.* 96:3147-3176 (1996).
Fish & Richardson P.C., RCE and IDS in Reply to Notice of Allowance of Dec. 2, 2010 in U.S. Appl. No. 10/569,065, filed Feb. 15, 2011, 5 pages.
Fish & Richardson P.C., Response to Notice of Allowance of Nov. 22, 2010 in U.S. Appl. No. 11/571,707, filed Feb. 18, 2011, 12 pages.
USPTO Office Action in U.S. Appl. No. 12/089,275, mailed Jan. 26, 2011, 25 pages.

* cited by examiner

BIPHENYLOXYACETIC ACID DERIVATIVES FOR THE TREATMENT OF RESPIRATORY DISEASE

CROSS-REFERENCE TO RELATED APPLICATIONS

This application is a national phase application under 35 U.S.C. §371 of PCT International Application No. PCT/GB2006/003697, filed Oct. 5, 2006, which claims the benefit of United Kingdom Application Serial No. 0520324.5, filed Oct. 6, 2005, United Kingdom Application Serial No. 0525082.4, filed Dec. 9, 2005 and United Kingdom Application Serial No. 0602800.5, filed Feb. 11, 2006. Each of these prior applications is incorporated herein by reference in its entirety.

The present invention relates to substituted phenoxyacetic acids as useful pharmaceutical compounds for treating respiratory disorders, pharmaceutical compositions containing them, and processes for their preparation.

WO2004089884 and WO2004089885 disclose a series of phenoxyacetic acids that are active at the CRTh2 receptor. It has now been found that certain compounds within the generic scopes of WO2004089884 and WO2004089885, but not specifically disclosed therein, exhibit surprisingly high potency at the CRTh2 receptor together with excellent pharmacokinetic properties in animal species, and as a consequence are expected to be potentially useful for the treatment of various respiratory diseases, including asthma and COPD.

In a first aspect the invention therefore provides a compound of formula (I) or a pharmaceutically acceptable salt thereof:

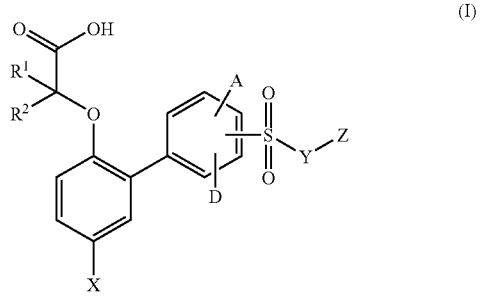

(I)

in which:

A and D are independently selected from hydrogen, halogen, nitrile, $C_{1-3}$ alkyl, $C_{1-3}$ alkoxy (the latter 2 groups can be optionally substituted by one or more halogen atoms); X is halogen, or $C_{1-3}$ alkyl which is optionally substituted by one or more halogen atoms; Y is a bond;

Z is aryl or heteroaryl substituted by one or more selected from hydrogen, halogen, nitrile, $C_{1-6}$ alkyl, $C_{1-6}$ alkoxy, $SO_2C_{1-6}$alkyl, heteroaryl; the latter four groups may be optionally substituted by halogen atoms, nitrile or $SO_2C_{1-6}$alkyl;

$R^1$ and $R^2$ independently represent a hydrogen atom, or a $C_{1-3}$ alkyl group;

or $R^1$ and $R^2$ together can form a 3-8 membered ring optionally containing one or more atoms selected from O, S, $NR^3$ and itself optionally substituted by one or more $C_1$-$C_3$ alkyl; and $R^3$ is hydrogen or $C_1$-$C_6$ alkyl.

In the context of the present specification, unless otherwise indicated, an alkyl group or an alkyl moiety in a substituent group may be linear or branched.

Aryl is defined as phenyl, napthyl or biphenyl;

Heteroaryl is defined as a 5-7 member aromatic ring or can be 6,6- or 6,5-fused bicyclic ring optionally containing one or more heteroatoms selected from N, S, O. The bicyclic ring may be linked through carbon or nitrogen and may be attached through the 5 or 6 membered ring and can be fully or partially saturated.

Examples include pyridine, pyrimidine, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, benzoxazole, purine, 4H-quinolizine, cinnoline, phthalazine, quinazoline, quinoxaline, 1,8-naphthyridine, pteridine, quinolone and 1,2-methylenedioxy benzene.

Preferably X is chloro, fluoro or methyl.

Preferably the group $SO_2$—Y—Z is at the 4-position of the phenyl ring:—

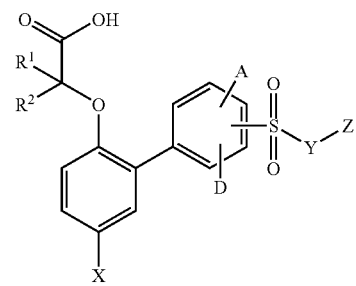

More preferably the group $SO_2$—Y—Z is at the 4-position of the phenyl ring, ortho to both group A and group D:—

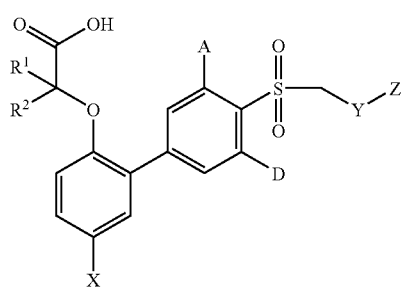

Most preferably the group $SO_2$—Y—Z is at the 4-position of the phenyl ring, ortho to the group A and meta to the group D:—

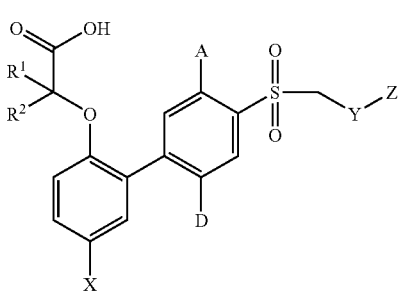

Preferably the groups A and D are independently hydrogen, halogen or $C_{1-3}$ alkyl (the latter being optionally substituted by halogen atoms); more preferably A is hydrogen, halogen or $CF_3$; D is hydrogen, halogen or methyl; most preferably A and D are independently selected from hydrogen and halogen.

Preferably $R^1$ and $R^2$ are independently hydrogen or $C_{1-3}$ alkyl, more preferably hydrogen or methyl.

Preferably Y is a bond.

Preferably Z is phenyl optionally substituted by halogen or $C_{1-6}$ alkoxy; more preferably Z is phenyl optionally substituted by halogen; most preferably Z is phenyl optionally substituted by fluoro.

Preferred compounds of the invention include:
{5-Chloro-4'-(phenylsulfonyl)biphenyl-2-yl]oxy}acetic acid;
{[3',5-Difluoro-4'-(phenylsulfonyl)biphenyl-2-yl]oxy}acetic acid;
(2S)-2-{[3',5-Difluoro-4'-(phenylsulfonyl)biphenyl-2-yl]oxy}propanoic acid;
({5-Chloro-3'-fluoro-4'-[(4-fluorophenyl)sulfonyl]biphenyl-2-yl}oxy)acetic acid;
{[2',5-Difluoro-4'-(phenylsulfonyl)biphenyl-2-yl]oxy}acetic acid;
{[5-Chloro-2'-fluoro-4'-(phenylsulfonyl)biphenyl-2-yl]oxy}acetic acid;
{[5-fluoro-4'-(phenylsulfonyl)-3'-(trifluoromethyl)biphenyl-2-yl]oxy}acetic acid;
(2S)-2-({5-chloro-4'-[(4-fluorophenyl)sulfonyl]biphenyl-2-yl}oxy)propanoic acid;
({5-chloro-2'-fluoro-4'-[(4-fluorophenyl)sulfonyl]biphenyl-2-yl}oxy)acetic acid;
(2S)-2-({5-chloro-2'-fluoro-4'-[(4-fluorophenyl)sulfonyl]biphenyl-2-yl}oxy)propanoic acid;
(2S)-2-({3',5-difluoro-4'-[(2-fluorophenyl)sulfonyl]biphenyl-2-yl}oxy)propanoic acid;
(2S)-2-({3',5-difluoro-4'-[(4-methoxyphenyl)sulfonyl]biphenyl-2-yl}oxy)propanoic acid;
(2S)-2-({3',5-difluoro-4'-[(3-fluorophenyl)sulfonyl]biphenyl-2-yl}oxy)propanoic acid;
({5-chloro-4'-[(4-fluorophenyl)sulfonyl]-2'-methylbiphenyl-2-yl}oxy)acetic acid;
(2S)-2-{[2'-chloro-5-fluoro-4'-(phenylsulfonyl)biphenyl-2-yl]oxy}propanoic acid;
({3'-fluoro-4'-[(4-fluorophenyl)sulfonyl]-5-methylbiphenyl-2-yl}oxy)acetic acid;
({5-chloro-4'-[(4-methoxyphenyl)sulfonyl]biphenyl-2-yl}oxy)acetic acid;
({4'-[(2-chlorophenyl)sulfonyl]-3',5-difluorobiphenyl-2-yl}oxy)acetic acid;
(2S)-2-{[3'-chloro-5-fluoro-4'-(phenylsulfonyl)biphenyl-2-yl]oxy}propanoic acid;
({4'-[(3-chlorophenyl)sulfonyl]-2',5-difluorobiphenyl-2-yl}oxy)acetic acid;
({2'-fluoro-4'-[(4-fluorophenyl)sulfonyl]-5-methylbiphenyl-2-yl}oxy)acetic acid;
{[3'-fluoro-5-methyl-4'-(phenylsulfonyl)biphenyl-2-yl]oxy}acetic acid;
{[5-chloro-3',5'-difluoro-4'-(phenylsulfonyl)biphenyl-2-yl]oxy}acetic acid
and pharmaceutically acceptable salts thereof.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compound of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, tertiarybutylamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

It will be appreciated by those skilled in the art that in the processes of the present invention certain functional groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Compounds of formula (I) can be prepared by hydrolysis of a compound of formula (II):

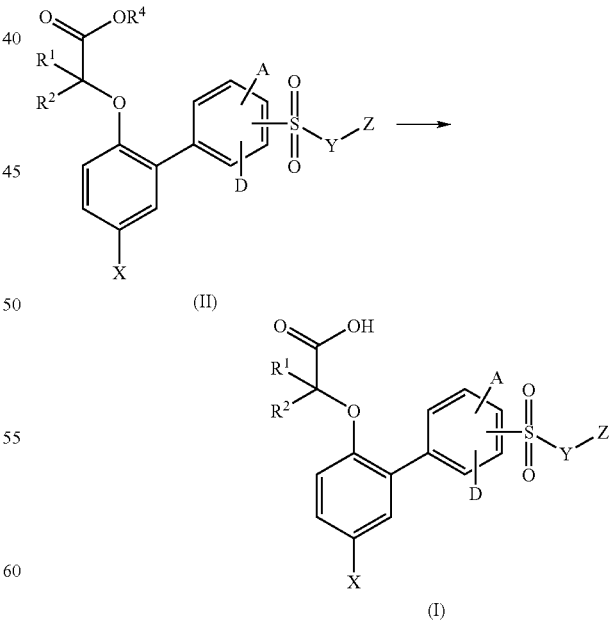

in which X, A, D, Y, Z, $R^1$ and $R^2$ are as defined in formula (I) or are protected derivatives. $R^4$ is $C_1-C_{10}$ alkyl group. Suitable groups $R^4$ include methyl, ethyl or tert-butyl. Hydrolysis of the ester group $R^4$ can be carried out using routine procedures, for example treatment of methyl and ethyl esters with aqueous sodium hydroxide, and treatment of tert-butyl esters with acids such as trifluoroacetic acid.

Compounds of formula (II) can be prepared by reaction of a compound of formula (III) with a compound of formula (IV):

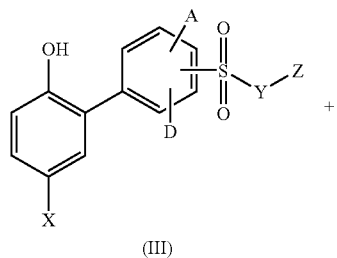

(III)

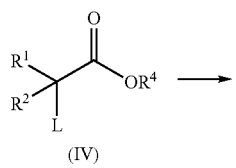

(IV)

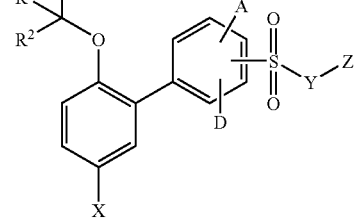

(II)

in which X, A, D, Y, Z, $R^1$, $R^2$ are as defined in formula (I) or are protected derivatives. L is a suitable leaving group such as halo or an activated alcohol, in particular chlorine, bromine or tosylate. The reaction can be carried out in a suitable solvent such as acetonitrile or DMF using a base such as potassium carbonate or the like. L may also be hydroxy so that a Mitsunobu reaction may be performed with compound (II) using for example triphenylphosphine and diethyl azodicarboxylate. Compounds of formula (II) are novel and form an additional part of this invention.

Compounds of formula (III) can be prepared by deprotection of a compound of formula (V):

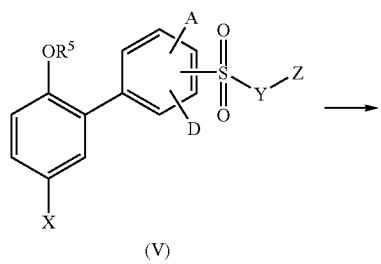

(V)

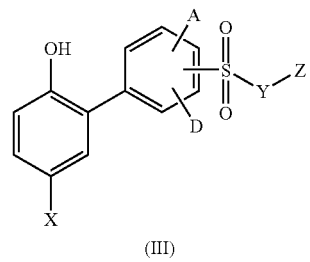

(III)

in which X, A, D, Y and Z, are as defined in formula (I) or are protected derivatives. $R^5$ is a suitable protecting group, for example benzyl or $C_{1-6}$ alkyl, such as methyl. The protecting group $R^5$ can be removed using a suitable dealkylating agent such as $BBr_3$ in a suitable solvent such as DCM or the like. If $R^5$ is benzyl, then it can also be removed using standard hydrogenation conditions, such as palladium on charcoal in a suitable organic solvent under an atmosphere of hydrogen in a sealed vessel. Compounds of formula (V) are novel and form an additional part of this invention.

Compounds of formula (III) and compounds of formula (V) can be prepared by reaction of a compound of formula (VI) or a compound of formula (VII) with a compound of formula (VIII) via a Suzuki coupling reaction followed by deprotection of $R^5$:

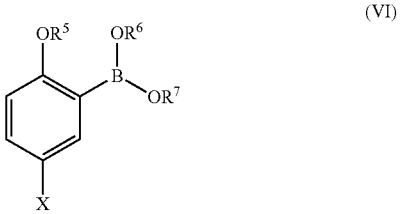

(VI)

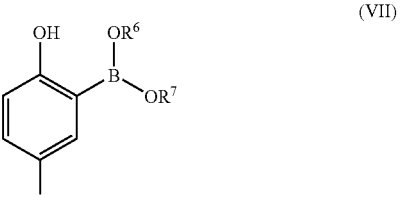

(VII)

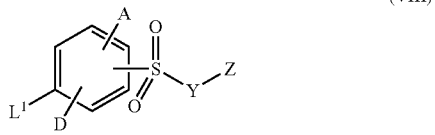

(VIII)

in which X, A, D, Y and Z, are as defined in formula (I) or are protected derivatives thereof, $R^5$ as defined for compounds of formula (V). $L^1$ is a suitable leaving group such as halo or an activated alcohol; suitably bromo, iodo or triflate. Compounds of formula (VI) are commercially available or can be prepared as outlined previously in WO2004089884 and WO2004089885.

The above steps can also be reversed. For example, compounds of formula (V) can be prepared by reacting compounds of formula (VIa) with a compound of formula (VIIIa) using a suzuki coupling reaction followed by removal of the protecting group as outlined above.

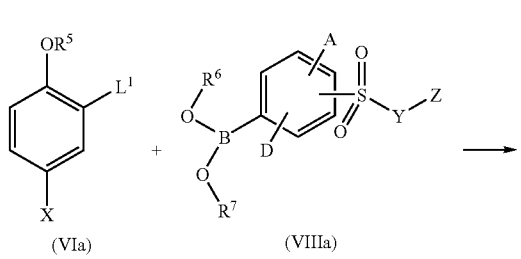

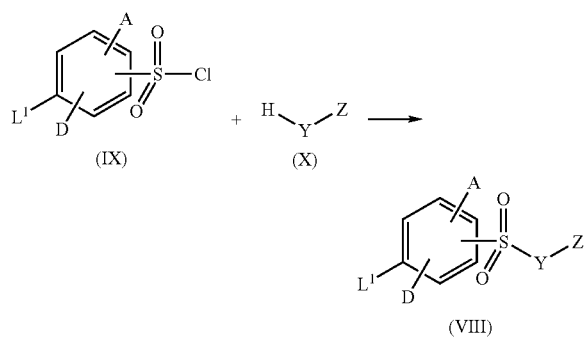

in which X, A, D, Y and Z, are as defined in formula (I) or are protected derivatives thereof, $L^1$, $R^5$ and $R^6$ are as outlined above.

Compounds of formula (VIII) can be prepared by reacting compounds of formula (IX) with compounds of formula (X):

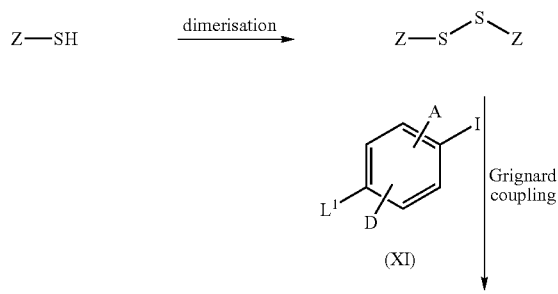

in which A, D, Y and Z, are as defined in formula (I) or are protected derivatives thereof, $L^1$, is as outlined above.

The reaction can be carried out in a microwave at elevated temperatures or can be performed thermally by heating a compound of formula (IX) with a compound of formula (X) at elevated temperatures such as refluxing conditions. The reactions are carried out using a Lewis acid catalyst, such as iron (III) chloride.

Compounds of formula (VIII) can also be formed as outlined below:

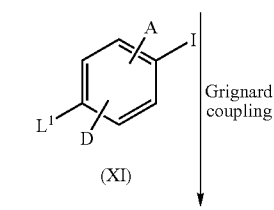

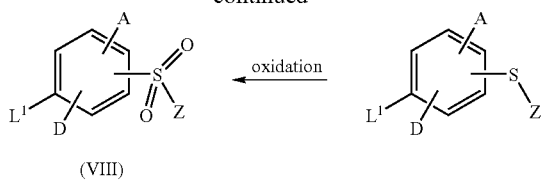

in which A, D and Z, are as defined in formula (I) or are protected derivatives thereof, $L^1$, is a suitable leaving group as outlined above. The thiol is dimerised by reacting with sulfuryl chloride in a suitable organic solvent such as dichloromethane at low temperatures, preferably 0° C. Alternatively the thiol is dimerised by reacting with hexamethyldisilazane and DMSO in a suitable organic solvent such as acetonitrile. The disulfide product can then be reacted with aryl halides, in particular aryl iodides compounds of formula (XI) using standard Grignard coupling conditions. The resulting sulfide can then be oxidised using standard oxidising procedures known by those skilled in the art, such as reacting with mCPBA in dichloromethane or the like.

Alternatively, compounds of formula (VIII) can also be formed from the disulfide by reaction with an aniline of formula (VIV) using diazotisation conditions, preferably using isoamyl nitrite in a suitable solvent such as acetonitrile or the like at elevated temperatures. The resulting sulfide was oxidised as outlined above.

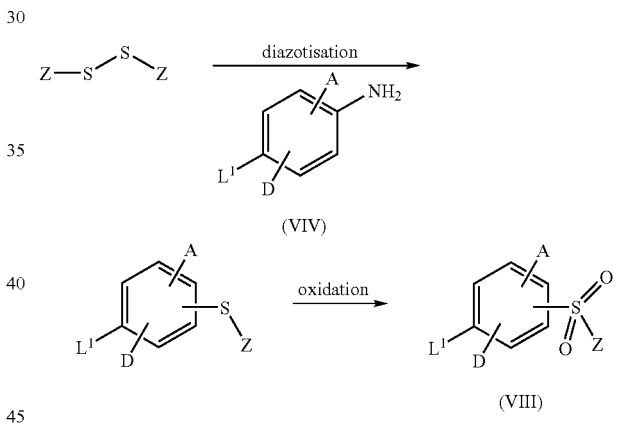

in which A, D and Z, are as defined in formula (I) or are protected derivatives thereof, $L^1$, is a suitable leaving group as outlined above.

Compounds of formula (VIV) are commercially available or can be readily prepared using literature procedures by those skilled in the art.

In a further aspect, the present invention provides the use of a compound of formula (I), a prodrug, pharmaceutically acceptable salt or solvate thereof for use in therapy.

The compounds of formula (I) or pharmaceutically acceptable slats thereof have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites.

A compound of the invention, or a pharmaceutically acceptable salt thereof, can be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthropathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosis et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani: coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinophilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

16. Diseases associated with raised levels of $PGD_2$ or its metabolites.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

In a further aspect, the present invention provides the use of a compound of formula (I), or a pharmaceutically acceptable salt or solvate thereof, as hereinbefore defined in the manufacture of a medicament for use in therapy.

In a further aspect, the present invention provides the use of a compound or formula (I), or a pharmaceutically acceptable salt or solvate thereof, as hereinbefore defined in the manufacture of a medicament for use in therapy in combination with drugs used to treat asthma and rhinitis (such as inhaled and oral steroids, inhaled β2-receptor agonists and oral leukotriene receptor antagonists).

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below:

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-1) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAYx1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlulcast (MK-679), RG-12525, Ro-245913, iralukast (CGP 45715A), and BAYx7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenytoin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; or (xxvii) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:
(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);
(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;
(iii) an agent which inhibits cancer cell invasion (for example a metalloproteinase inhibitor like marimastat or an inhibitor of urokinase plasminogen activator receptor function);
(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholino propoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy) quinazolin-4-amine (CI 1033)), an inhibitor of the platelet-derived growth factor family, or an inhibitor of the hepatocyte growth factor family;
(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;
(vii) an agent used in antisense therapy, for example one directed to one of the targets listed above, such as ISIS 2503, an anti-ras antisense;
(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or
(ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The invention will now be illustrated by the following non-limiting examples in which, unless stated otherwise:

(i) when given, $^1$H NMR data is quoted in the form of delta values for major diagnostic protons, given in parts per million (ppm) relative to tetramethylsilane (TMS) as an internal standard;

(ii) mass spectra (MS): generally only ions which indicate the parent mass are reported, unless otherwise indicated;

(iii) the title compounds of the examples and methods were named according to IUPAC rules using the ACD/name and ACD/name batch (version 8.0) from Advanced Chemical Development Inc, Canada;

(iv) unless stated otherwise, reverse phase HPLC was conducted using a Symmetry, NovaPak or Ex-Terra reverse phase silica column;

(v) solvents were dried with $MgSO_4$ or $Na_2SO_4$ (vi) the following abbreviations are used:

| | |
|---|---|
| EtOAc | ethylacetate |
| Ether | diethyl ether |
| $MgSO_4$ | anhydrous magnesium sulfate |
| $Na_2SO_4$ | anhydrous sodium sulfate |
| HCl | hydrochloric acid |
| DCM | dichloromethane |
| DMSO | dimethylsulfoxide |
| h | hour |
| MCPBA | 3-chloroperoxybenzoic acid (Aldrich 77% max) |
| min | minutes |
| $NaHCO_3$ | sodium hydrogen carbonate |
| TFA | trifluoroacetic acid |
| $Pd(dppf)Cl_2$ | [1,1'-Bis(diphenylphosphino)ferrocene]dichloropalladium (II), complex with dichloromethane |
| THF | tetrahydrofuran |
| NaOH | sodium hydroxide |
| RT | room temperature |

EXAMPLE 1

{[5-Chloro-4'-(phenylsulfonyl)biphenyl-2-yl]oxy}acetic acid

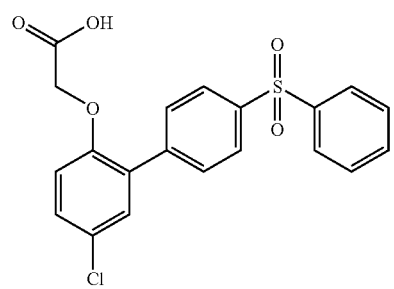

(i) 2'-(Benzyloxy)-5'-chlorobiphenyl-4-yl phenyl sulfone

5-Chloro-2-(phenylmethoxy)phenyl]-boronic acid (prepared by the method of WO2004089885A1) (0.5 g) in dioxan (20 ml) was treated with 1-bromo-4-(phenylsulfonyl)benzene (0.57 g) prepared by the method used in JACS (1952), 74, 394-7. Sodium carbonate (0.40 g) and palladium(diphenylphosphinoferrocene)dichloride (0.070 g) were added and the mixture heated to 80° C. for 16 hours. The mixture was diluted with water, extracted with ethyl acetate, dried and evaporated under reduced pressure to give an oil. The oil was purified by chromatography on silica eluting with isohexane/diethylether 2:1 to give the sub-title compound as a white solid, yield 0.9 g.

$^1$H-NMR $CDCl_3$: δ 8.00-7.92 (4H, m), 7.67-7.49 (5H, m), 7.30-7.19 (7H, m), 7.02-6.95 (1H, d), 5.08 (2H, s).

(ii) 5-Chloro-4'-(phenylsulfonyl)biphenyl-2-ol

The product from example 1 step (i) (0.9 g) was treated with 1.0M boron tribromide in DCM (3.10 ml) in dry DCM (20 ml) and stirred at room temperature for 1 hour. The mixture was quenched in ice water and extracted with DCM, dried ($MgSO_4$) and concentrated under reduced pressure to give the sub-title compound, yield 0.9 g MS: ESI(−ve) 343 (M−1)

(iii) tert-Butyl {[5-chloro-4'-(phenylsulfonyl)biphenyl-2-yl]oxy}acetate

A flask was charged with tert-butylbromoacetate (0.42 ml), dry DMF (20 ml), potassium carbonate (0.36 g) and the product from example 1 step (ii) (0.9 g) and then stirred at room temperature overnight. The mixture was quenched in water and extracted with diethylether, dried ($MgSO_4$) and concentrated under reduced pressure to give an oil. The oil was purified by chromatography on silica eluting with isohexane/diethylether 2:1 to give the sub-title compound as a colourless oil, yield 0.6 g.

MS: ESI(+ve) 476 (M+$NH_4$)

(iv) {5-Chloro-[4'-(phenylsulfonyl)biphenyl-2-yl]oxy}acetic acid

The title compound was prepared from the product of step (iii) (0.6 g) which was stirred in TFA/DCM (1:1, 10 ml)

overnight. The mixture was concentrated under reduced pressure to give an oil. The residue was purified by reverse phase HPLC, yield 0.31 g.

$^1$H NMR: DMSO-d6: δ 8.03-7.62 (9H, m), 7.42-7.39 (2H, m), 7.08-7.05 (1H, d), 4.74 (2H, s).

MS: ESI(−ve) 401 (M−1)

EXAMPLE 2

{[3,5-Difluoro-4'-(phenylsulfonyl)biphenyl-2-yl]oxy}acetic acid

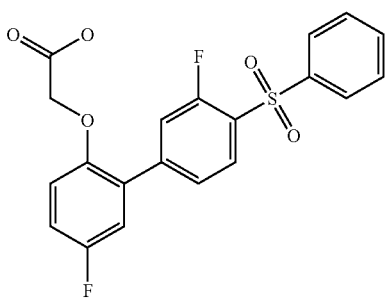

(i) 4-Bromo-2-fluoro-1-(phenylsulfonyl)benzene

4-Bromo-2-fluoro-benzenesulfonyl chloride (2 g), benzene (1.3 ml) and iron (III) chloride (35 mg) were heated in a sealed tube using a microwave at 200 Watts for 15 seconds. After cooling purification by flash column chromatography (eluent 20% EtOAc/Hexane) gave the subtitle compound as a solid, yield 1.8 g.

$^1$H NMR DMSO-d6: δ 8.03-7.95 (3H, m), 7.84 (1H, dd), 7.80-7.65 (4H, m)

(ii) 3',5-Difluoro-2-methoxy-4'-(phenylsulfonyl)biphenyl

To a solution/suspension of the product from part (i) (0.55 g), 5-fluoro-2-methoxy-phenylboronic acid (0.3 g) in toluene (6 ml), ethanol (4 ml) and 2M Na$_2$CO$_3$ (3 ml) was added tetrakis(triphenylphosphine)palladium (0.05 g). The mixture was heated to 85° C. for 3 h, concentrated under reduced pressure to give a crude material. The residue was suspended in water, extracted with ethylacetate, washed with brine, dried (MgSO$_4$) and concentrated under reduced pressure. Purification using flash column chromatography (eluent 10% diethylether/hexane) gave the subtitle compound, yield 0.39 g.

$^1$H NMR DMSO-d6: δ 8.08 (1H, t), 8.00 (2H, d), 7.81-7.55 (5H, m), 7.28 (2H, m), 7.17 (1H, m), 3.77 (3H, s).

(iii) 3',5-Difluoro-4'-(phenylsulfonyl)biphenyl-2-ol

The product from step ii) (0.44 g) was treated with 1.0M boron tribromide in DCM (3.7 ml) in DCM (10 ml) and stirred at 0° C. for 18 h. The mixture was quenched in ice water and extracted with EtOAc; dried (MgSO$_4$) and concentrated in vacuo to give the sub-title compound, yield 0.39 g.

$^1$H NMR DMSO-d6: δ 9.97 (1H, s), 8.07 (1H, t), 7.99 (2H, d), 7.80-7.60 (5H, m), 7.25 (1H, m), 7.10 (1H, m), 6.96 (1H, m).

(iv) tert-Butyl {[3',5-difluoro-4'-(phenylsulfonyl)biphenyl-2-yl]oxy}acetate

The subtitle compound was prepared by the method of example 1 step (iii) using the product from step (iii).

$^1$H NMR DMSO-d6: δ 8.09 (1H, t), 8.00 (2H, d), 7.80-7.65 (5H, m), 7.34 (1H, m), 7.25 (1H, m), 7.07 (1H, m), 4.71 (2H, s), 1.37 (9H, s).

(v) {[3',5-Difluoro-4'-(phenylsulfonyl)biphenyl-2-yl]oxy}acetic acid

The title compound was prepared by the method of example 1 step (iv) using the product from part (iv).

$^1$H NMR DMSO-d6: δ 13.08 (1H, s), 8.08 (1H, t), 8.00 (2H, d), 7.80-7.66 (5H, m), 7.33 (1H, m), 7.24 (1H, m), 7.09 (1H, m), 4.75 (2H, s).

MS: APCI−ve 403 (M−1)

EXAMPLE 3

(2S)-2-{[3',5-Difluoro-4'-(phenylsulfonyl)biphenyl-2-yl]oxy}propanoic acid

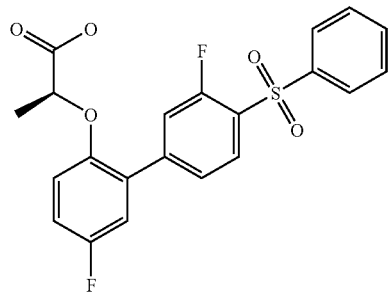

(i) tert-Butyl (2S)-2-{[3',5-difluoro-4'-(phenylsulfonyl)biphenyl-2-yl]oxy}propanoate Diisopropyl azodicarboxylate (0.19 ml) was added to a solution of the product of example 2 part (iii) (250 mg), tert-butyl (R)-(+)-lactate (141 mg) and triphenylphosphine (252 mg) in tetrahydrofuran (10 ml) at 0° C. After 20 minutes the ice bath was removed and the reaction stirred at room temperature overnight. The reaction mixture was then adsorbed onto silica and purified using flash column chromatography (eluent 10% ethylacetate/hexane) to give the subtitle compound as an oil, yield 140 mg.

$^1$H NMR DMSO-d6: δ 8.09 (1H, t), 8.00 (2H, m), 7.81-7.66 (5H, m), 7.34 (1H, m), 7.24 (1H, m), 7.02 (1H, m), 4.91 (1H, q), 1.40 (3H, d), 1.34 (9H, s).

(ii) (2S)-2-{[3',5-Difluoro-4'-(phenylsulfonyl)biphenyl-2-yl]oxy}propanoic acid

The title compound was prepared by the method of example 1 step (iv) using the product from step (i).

$^1$H NMR DMSO-d6: δ 8.08 (1H, t), 8.00 (2H, d), 7.80-7.67 (5H, m), 7.33 (1H, m), 7.23 (1H, m), 7.02 (1H, m), 4.95 (1H, q), 1.42 (3H, d).

MS: APCI−ve 417 (M−1)

EXAMPLE 4

({5-Chloro-3'-fluoro-4'-[(4-fluorophenyl)sulfonyl]biphenyl-2-yl}oxy)acetic acid

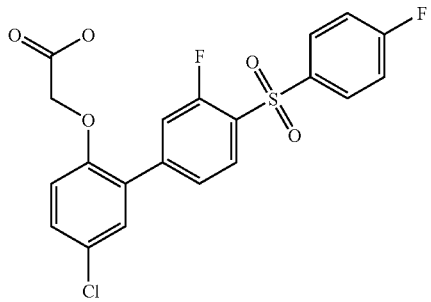

i) 4-Bromo-2-fluoro-1-[(4-fluorophenyl)sulfonyl]benzene

The subtitle compound was prepared by the method of example 2 step (i) using 4-bromo-2-fluorobenzenesulfonyl chloride and fluorobenzene.

$^1$H NMR DMSO-d6: δ 8.04 (2H, m), 7.99 (1H, t), 7.86 (1H, d), 7.75 (1H, dd), 7.51 (2H, m).

ii) 5-Chloro-3'-fluoro-4'-[(4-fluorophenyl)sulfonyl]-2-methoxybiphenyl

The subtitle compound was prepared by the method of example 2 step (ii) using the product of step (i) and 5-chloro-2-methoxyphenyl boronic acid.

$^1$H NMR DMSO-d6: δ 8.1-8.05 (3H, m), 7.65-7.44 (6H, m), 7.19 (1H, d), 3.78 (3H, s).

iii) 5-Chloro-3'-fluoro-4'-[(4-fluorophenyl)sulfonyl]biphenyl-2-ol

The subtitle compound was prepared by the method of example 2 step (iii) using the product of step (ii).

$^1$H NMR DMSO-d6: δ 10.27 (1H, s), 8.09-8.04 (3H, m), 7.7 (1H, dd), 7.63 (1H, dd), 7.52 (2H, m), 7.41 (1H, d), 7.29 (1H, dd), 6.99 (1H, d).

iv) tert-butyl ({5-Chloro-3'-fluoro-4'-[(4-fluorophenyl)sulfonyl]biphenyl-2-yl}oxy)acetate The subtitle compound was prepared by the method of example 1 step (iii) using the product of step (iii).

$^1$H NMR DMSO-d6: δ 8.11-8.05 (3H, m), 7.73-7.66 (2H, m), 7.56-7.43 (4H, m), 7.09 (1H, m), 4.74 (2H, s), 1.38 (9H, s).

v) ({5-Chloro-3'-fluoro-4'-[(4-fluorophenyl)sulfonyl]biphenyl-2-yl}oxy)acetic acid The title compound was prepared by the method of example 1 step (iv) using the product of step (iv).

$^1$H NMR DMSO-d6: δ 13.13 (1H, s), 8.10-8.05 (3H, m), 7.73 (1H, s), 7.7 (1H, dd), 7.53 (2H, dt), 7.49 (1H, d), 7.44 (1H, dd), 7.11 (1H, d), 4.78 (2H, s).

MS: APCI(−ve) 436 (M−1)

EXAMPLE 5

{[2',5-Difluoro-4'-(phenylsulfonyl)biphenyl-2-yl]oxy}acetic acid

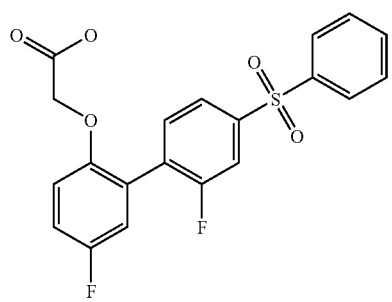

i) 1-Bromo-2-fluoro-4-(phenylsulfonyl)benzene

The subtitle compound was prepared by the method of example 2 step (i) using 4-bromo-3-fluorobenzenesulfonyl chloride and benzene.

$^1$H NMR DMSO-d6: δ 8.04-7.97 (4H, m), 7.74 (2H, m), 7.65 (2H, m).

ii) 2,5'-Difluoro-2'-methoxybiphenyl-4-yl phenyl sulfone

The subtitle compound was prepared by the method of example 2 step (ii) using the product of step (i) and 5-fluoro-2-methoxyphenylboronic acid.

$^1$H NMR DMSO-d6: δ 8.07 (2H, m), 7.91 (1H, dd), 7.85 (1H, dd), 7.75 (1H, m), 7.7-7.61 (3H, m), 7.29 (1H, m), 7.21 (1H, dd), 7.15 (1H, dd), 3.72 (3H, s).

iii) 2',5-Difluoro-4'-(phenylsulfonyl)biphenyl-2-ol

The subtitle compound was prepared by the method of example 2 step (iii) using the product of step (ii).

$^1$H NMR DMSO-d6: δ 9.77 (1H, s), 8.06 (2H, d), 7.89 (1H, d), 7.83 (1H, d), 7.78-7.63 (4H, m), 7.12 (2H, m), 6.93 (1H, m).

iv) {[2',5-Difluoro-4'-(phenylsulfonyl)biphenyl-2-yl]oxy}acetic acid

The title compound was prepared by the methods of example 1 step (iii) and example 1 step iv) using the product of step (iii).

$^1$H NMR DMSO-d6: δ 12.97 (1H, s), 8.07 (2H, m), 7.91 (1H, dd), 7.85 (1H, dd), 7.77-764 (4H, m), 7.29-7.21 (2H, m), 7.05 (1H, dd), 4.67 (2H, s).

MS: APCI(−ve) 403 (M−1)

EXAMPLE 6

{[5-Chloro-2'-fluoro-4'-(phenylsulfonyl)biphenyl-2-yl]oxy}acetic acid

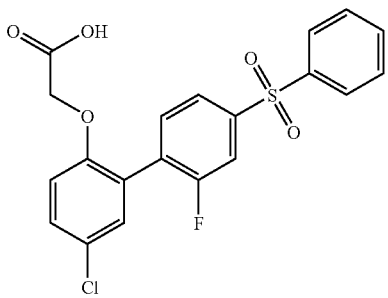

i) 5'-Chloro-2-fluoro-2'-methoxybiphenyl-4-yl phenyl sulfone

The subtitle compound was prepared by the method of example 2 step (ii) using the product of example 5 step (i) and 5-chloro-2-methoxybenzene boronic acid.

$^1$H NMR DMSO-d6: δ 8.08-8.05 (2H, m), 7.91 (1H, dd), 7.84 (1H, dd), 7.75 (1H, m), 7.7-7.62 (3H, m), 7.50 (1H, dd), 7.37 (1H, d), 7.17 (1H, d), 3.73 (3H, s).

ii) 5-Chloro-2'-fluoro-4'-(phenylsulfonyl)biphenyl-2-ol

The subtitle compound was prepared by the method of example 2 step (iii) using the product of step (i).

$^1$H NMR DMSO-d6: δ 10.09 (1H, s), 8.08-8.05 (2H, m), 7.89 (1H, dd), 7.83 (1H, dd), 7.77-7.72 (1H, m), 7.69-7.64 (3H, m), 7.32-7.27 (2H, m), 6.96 (1H, dd).

iii) {[5-Chloro-2'-fluoro-4'-(phenylsulfonyl)biphenyl-2-yl]oxy}acetic acid

The title compound was prepared by the methods of example 1 step (iii) and example 1 step (iv) using the product of step (ii).

$^1$H NMR DMSO-d6: δ 13.02 (1H, s), 8.09-8.06 (2H, m), 7.92 (1H, dd), 7.85 (1H, dd), 7.77-7.65 (4H, m), 7.46 (1H, d), 7.39 (1H, d), 7.06 (1H, d), 4.7 (2H, s).

MS: APCI(−ve) 419 (M−1)

EXAMPLE 7

{[5-fluoro-4'-(phenylsulfonyl)-3'-(trifluoromethyl)biphenyl-2-yl]oxy}acetic acid

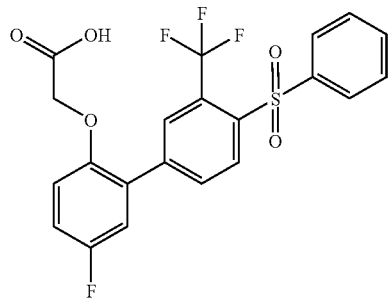

i) 4-bromo-1-(phenylsulfonyl)-2-(trifluoromethyl)benzene

The subtitle compound was prepared by the method of example 2 step (i) using 4-bromo-2-(trifluoromethyl)benzenesulfonyl chloride and benzene.

$^1$H NMR DMSO-d6: δ 8.35 (1H, d), 8.25 (1H, dd), 8.21 (1H, d), 7.88 (2H, d), 7.76-7.72 (1H, m), 7.67-7.62 (2H, m).

ii) 5'-fluoro-2'-methoxy-3-(trifluoromethyl)biphenyl-4-yl phenyl sulfone

The subtitle compound was prepared by the method of example 2 step (ii) using the product of step (i) and 5-fluoro-2-methoxybenzene boronic acid.

$^1$H NMR DMSO-d6: δ 8.47 (1H, d), 8.12 (1H, dd), 8.09 (1H, d), 7.92 (2H, d), 7.77-7.64 (3H, m), 7.40 (1H, dd), 7.31 (1H, td), 7.20 (1H, dd), 3.78 (3H, s).

iii) 5-fluoro-4'-(phenylsulfonyl)-3'-(trifluoromethyl biphenyl-2-ol

The subtitle compound was prepared by the method of example 2 step (iii) using the product of step (ii).

$^1$H NMR DMSO-d6: δ 10.06 (1H, s), 8.47 (1H, d), 8.21-8.15 (2H, m), 7.91 (2H, d), 7.77-7.62 (3H, m), 7.35 (1H, dd), 7.14 (1H, m), 6.99 (1H, dd).

iv) tert-butyl {[5-fluoro-4'-(phenylsulfonyl)-3'-(trifluoromethyl)biphenyl-2-yl]oxy}acetate The subtitle compound was prepared by the method of example 1 step (iii) using the product of step (iii).

$^1$H NMR DMSO-d6: δ 8.47 (1H, s), 8.25 (1H, d), 8.17 (1H, m), 7.92 (2H, d), 7.74 (1H, m), 7.66 (2H, m), 7.42 (1H, m), 7.28 (1H, m), 7.13 (1H, m), 4.74 (2H, s), 1.36 (9H, s).

v) {[5-fluoro-4'-(phenylsulfonyl)-3'-(trifluoromethyl)biphenol-2-yl]oxy}acetic acid The title compound was prepared by the method of example 1 step (iv) using the product of step (iv).

$^1$H NMR DMSO-d6: δ 13.10 (1H, s), 8.47 (1H, d), 8.31 (1H, d), 8.18 (1H, dd), 7.92 (2H, d), 7.74 (1H, m), 7.66 (2H, t), 7.42 (1H, dd), 7.28 (1H, td), 7.15 (1H, dd), 4.78 (2H, s).

MS: APCI(−ve) 453 (M−1)

EXAMPLE 8

(2S)-2-({5-chloro-4'-[(4-fluorophenyl)sulfonyl]biphenyl-2-yl}oxy)propanoic acid

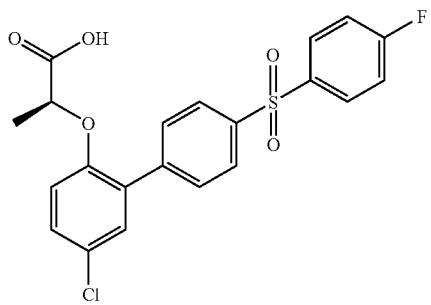

i) 4-bromophenyl 4-fluorophenyl sulfone

The subtitle compound was prepared by the method of example 2 step (i) using 4-fluorobenzenesulfonyl chloride and bromobenzene.

$^1$H NMR DMSO-d6: δ 8.1-8.02 (2H, m), 7.94-7.82 (4H, m), 7.53-7.44 (2H, m).

ii) 5-chloro-4'-[(4-fluorophenyl)sulfonyl]-2-methoxybiphenyl

The subtitle compound was prepared by the method of example 2 step (ii) using the product of step (i) and 5-chloro-2-methoxybenzene boronic acid.

$^1$H NMR DMSO-d6: δ 8.13-8.06 (2H, m), 8.00 (2H, dt), 7.73 (2H, dt), 7.54-7.38 (4H, m), 7.17 (1H, d), 3.76 (3H, s).

iii) 5-chloro-4'-[(4-fluorophenyl)sulfonyl]biphenyl-2-ol

The subtitle compound was prepared by the method of example 2 step (iii) using the product of step (ii).

$^1$H NMR DMSO-d6: δ 10.14 (1H, s), 8.14-8.07 (2H, m), 8.01 (2H, d), 7.81 (2H, d), 7.54-7.46 (2H, m), 7.36 (1H, d), 7.29 (1H, dd), 6.99 (1H, d).

iv) tert-butyl (2S)-2-({5-chloro-4'-[(4-fluorophenyl)sulfonyl]biphenyl-2-yl}oxy)propanoate The subtitle compound was prepared by the method of example 3 step (i) using the product of step (iii).

$^1$H NMR DMSO-d6: δ 8.15-8.10 (2H, m), 8.03 (2H, d), 7.88 (2H, d), 7.54-7.42 (4H, m), 7.03-6.99 (1H, m), 4.95 (1H, q), 1.41 (3H, d), 1.36 (9H, s).

v) (2S)-2-({5-chloro-4'-[(4-fluorophenyl)sulfonyl]biphenyl-2-yl}oxy)propanoic acid The title compound was prepared by the method of example 1 step (iv) using the product of step (iv).

$^1$H NMR DMSO-d6: δ 8.12-8.07 (2H, m), 8.0 (2H, d), 7.87 (2H, d), 7.49 (2H, t), 7.43-7.38 (2H, m), 7.0 (1H, d), 4.95 (1H, q), 1.41 (3H, d).

MS: APCI(−ve) 433 (M−1)

EXAMPLE 9

({5-chloro-2'-fluoro-4'-[(4-fluorophenyl)sulfonyl]biphenyl-2-yl}oxy)acetic acid

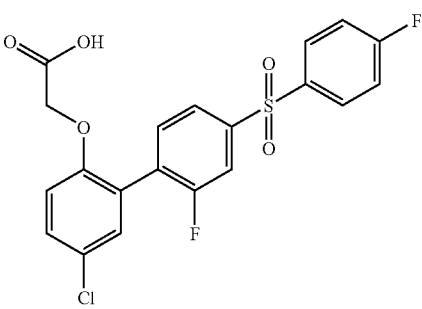

i) 1-bromo-2-fluoro-4-[(4-fluorophenyl)sulfonyl]benzene

Ferric chloride (0.5 g) was added to a mixture of 4-bromo-3-fluoro-benzenesulfonyl chloride (2.5 g) and fluorobenzene (3 ml) and then stirred at reflux for 18 hours. The flask was cooled to room temperature and the residue was partitioned between aqueous NaHCO$_3$ and DCM. The DCM layer was washed with brine, dried (MgSO$_4$) and evaporated under reduced pressure. The residue was recrystallised from ethanol to give buff coloured crystals.

$^1$H NMR DMSO-d6: δ 8.15-7.98 (4H, m), 7.76 (1H, dd), 7.56-7.46 (2H, m).

ii) 5'-chloro-2-fluoro-4-[(4-fluorophenyl)sulfonyl]-2'-methoxybiphenyl

The subtitle compound was prepared by the method of example 2 step (ii) using the product of step (i) and 5-chloro-2-methoxybenzene boronic acid.

$^1$H NMR DMSO-d6: δ 8.12 (2H, dddd), 7.9 (1H, dd), 7.82 (1H, dd), 7.62 (1H, t), 7.51-7.44 (3H, m), 7.33 (1H, d), 7.14 (1H, d), 3.7 (3H, s).

iii) 5-chloro-4'-[(4-fluorophenyl)sulfonyl]biphenyl-2-ol

The subtitle compound was prepared by the method of example 2 step (iii) using the product of step (ii).

$^1$H NMR DMSO-d6: δ 10.12 (1H, s), 8.2-8.14 (2H, m), 7.93 (1H, dd), 7.86 (1H, dd), 7.68 (1H, t), 7.52 (2H, t), 7.35-7.28 (2H, m), 6.98 (1H, d).

iv) tert-butyl ({5-chloro-2'-fluoro-4'-[(4-fluorophenyl)sulfonyl]biphenyl-2-yl}oxy)acetate The subtitle compound was prepared by the method of example 1 step (iii) using the product of step (iii).

$^1$H NMR DMSO-d6: δ 8.21-8.14 (2H, m), 7.95 (1H, dd), 7.89 (1H, dd), 7.74-7.68 (1H, m), 7.58-7.41 (4H, m), 7.05 (1H, d), 4.68 (2H, s), 1.36 (9H, s).

v) (2S)-2-({5-chloro-4'-[(4-fluorophenyl)sulfonyl]biphenyl-2-yl}oxy)propanoic acid The title compound was prepared by the method of example 1 step (iv) using the product of step (iv).

¹H NMR DMSO-d6: δ 8.18-8.13 (2H, m), 7.94 (1H, dd), 7.86 (1H, dd), 7.74-7.69 (1H, m), 7.54-7.48 (2H, m), 7.46 (1H, dd), 7.39 (1H, d), 7.06 (1H, d), 4.70 (2H, s).
MS: APCI(−ve) 437 (M−1)

EXAMPLE 10

(2S)-2-({5-chloro-2'-fluoro-4'-[(4-fluorophenyl)sulfonyl]biphenyl-2-yl}oxy)propanoic acid

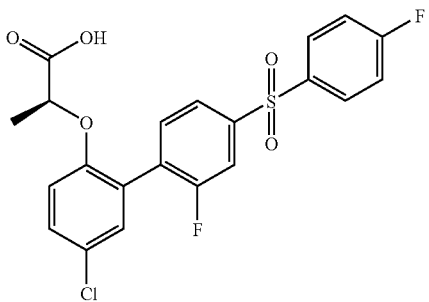

i) tert-butyl (2S)-2-({5-chloro-2'-fluoro-4'-[(4-fluorophenyl)sulfonyl]biphenyl-2-yl}oxy)propanoate The subtitle compound was prepared by the method of example 3 step (i) using the product of example 9 step (iii).
¹H NMR DMSO-d6: δ 8.21-8.14 (2H, m), 7.96 (1H, dd), 7.89 (1H, dd), 7.78-7.73 (1H, m), 7.56-7.46 (3H, m), 7.42 (1H, d), 7.0 (1H, d), 4.88 (1H, q), 1.36-1.33 (12H, m).

ii) (2S)-2-({5-chloro-2'-fluoro-4'-[(4-fluorophenyl)sulfonyl]biphenyl-2-yl}oxy)propanoic acid The title compound was prepared by the met-hod of example 1 step (iv) using the product of step (ii).
¹H NMR DMSO-d6: δ 8.18-8.12 (2H, m), 7.93 (1H, dd), 7.87-7.79 (2H, m), 7.53-7.47 (2H, m), 7.42 (1H, dd), 7.37 (1H, d), 6.97 (1H, d), 4.78 (1H, q), 1.31 (3H, s).
MS: APCI(−ve) 451 (M−1)

EXAMPLE 11

(2S)-2-({3',5-difluoro-4'-[(2-fluorophenyl)sulfonyl]biphenyl-2-yl}oxy)propanoic acid

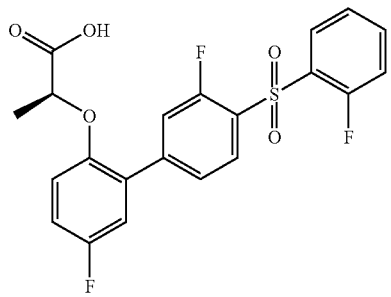

i) 1,1'-dithiobis(2-fluorobenzene)

Sulfuryl chloride (0.7 ml) was added dropwise to a solution of 2-fluorobenzenethiol (1.5 ml) in DCM (20 ml) at 0° C. The reaction mixture was stirred for 30 min, then concentrated under reduced pressure. The residue was purified by chromatography on silica eluting with isohexane to give the sub-title compound as an oil, yield 1.7 g.
MS: APCI(+ve) 254 (M+H)

ii)
4-bromo-2-fluoro-1-[(2-fluorophenyl)thio]benzene

4-Bromo-2-fluoro-1-iodobenzene (1.67 g) was added to a solution of isopropylmagnesium chloride (2.79 ml, 2M solution in THF) in THF (8 ml), which was cooled to 0° C. and stirred for a further 2 h. The mixture was then added to a solution of the product of step (i) in THF (5 ml). The reaction was allowed to reach RT overnight, then stirred at 40° C. for 1 hour and 50° C. for a further 1 hour. The reaction was cooled to RT, diluted with ammonium chloride and extracted with diethylether. The diethylether fractions were dried (MgSO₄) and evaporated under reduced pressure, yield 1.9 g. Used directly without further purification.
MS: APCI(+ve) 302 (M+H)

iii) 4-bromo-2-fluoro-1-[(2-fluorophenyl)sulfonyl]benzene

MCPBA (2.58 g) was added to a solution of the product of step ii) (1.8 g) in DCM (25 ml) at 0° C. The reaction mixture was allowed to reach RT and stirred for 23 hours. The reaction was washed with aqueous sodium metabisulfite, aqueous NaHCO₃, dried (MgSO₄) and then evaporated under reduced pressure. The residue was purified by chromatography on silica eluting with isohexane then 4:1 isohexane/ethyl acetate to give the sub-title compound as a white solid, yield 0.71 g.
¹H NMR CDCl₃: δ 8.16 (1H, t), 8.05 (1H, t), 7.67-7.62 (1H, m), 7.53 (1H, d), 7.37 (1H, d), 7.31 (1H, d), 7.13 (1H, t).

iv) 3',5-difluoro-4'-[(2-fluorophenyl)sulfonyl]-2-methoxybiphenyl

The subtitle compound was prepared by the method of example 2 step (ii) using the product of step (iii) and 5-fluoro-2-methoxybenzene boronic acid.
¹H NMR DMSO-d6: δ 8.12 (2H, dddd), 7.9 (1H, dd), 7.82 (1H, dd), 7.62 (1H, t), 7.51-7.44 (3H, m), 7.33 (1H, d), 7.14 (1H, d), 3.7 (3H, s).

v) 3',5-difluoro-4'-[(2-fluorophenyl)sulfonyl]biphenyl-2-ol

The subtitle compound was prepared by the method of example 2 step (iii) using the product of step (iv).
MS: APCI(−ve) 363 (M−H)

vi) methyl (2R)-2-{[(4-methylphenyl)sulfonyl]oxy}propanoate

A solution of methyl (R)-(+)-lactate (6.66 g) in acetonitrile (33 ml) was cooled to 5° C. and triethylamine (9.8 ml) added followed by trimethylamine hydrochloride (0.62 g). A separate solution of p-toluenesulfonyl chloride (11.6 g) in acetonitrile (33 ml) was added dropwise over 20 min maintaining the temperature below 5° C. The reaction mixture was filtered and concentrated. Diethylether and water were added and the organic fraction dried (MgSO₄) and concentrated in vacuo to give the sub-title compound as a yellow oil (13.71 g).

¹H NMR CDCl₃: δ 7.82 (2H, d), 7.35 (2H, d), 4.95 (1H, q), 3.67 (3H, s), 2.45 (3H, s), 1.51 (3H, d).

vii) methyl (2S)-2-({3',5-difluoro-4'-[(2-fluorophenyl)sulfonyl]biphenyl-2-yl}oxy)propanoate The product of step (v) (175 mg), the product of step (vi) (124 mg) and potassium carbonate (133 mg) in acetonitrile (10 ml) were charged to a flask and stirred at 65° C. overnight. The reaction mixture was cooled, diluted with water (20 ml) and extracted with diethyl ether. The combined organic extracts were washed with brine, dried (MgSO₄) and concentrated under reduced pressure. The residue was purified by chromatography on silica eluting with isohexane then 4:1 isohexane/ethyl acetate to give the sub-title compound as a colourless oil, yield 121 mg.
MS: APCI(+ve) 451 (M+H)

viii) (2S)-2-({3',5-difluoro-4'-[(2-fluorophenyl)sulfonyl]biphenyl-2-yl}oxy)propanoic acid The product of step (vii) (121 mg), 1M NaOH (0.4 ml), THF (2 ml) and DCM (2 ml) were charged to a flask and stirred for 3 hours and then concentrated under reduced pressure. The residue was dissolved in EtOAc, washed with 1M HCl. The organic phase was dried (MgSO₄) and concentrated under reduced pressure to give the title compound as a white solid, yield 63 mg.
¹H NMR DMSO-d6: δ 8.12 (2H, q), 7.89-7.8 (2H, m), 7.75 (1H, dd), 7.56 (1H, t), 7.47 (1H, dd), 7.36 (1H, dd), 7.24 (1H, td), 7.03 (1H, dd), 4.96 (1H, q), 1.43 (3H, d).
MS: APCI(−ve) 435 (M−H)

EXAMPLE 12

(2S)-2-({3',5-difluoro-4'-[(4-methoxyphenyl)sulfonyl]biphenyl-2-yl}oxy)propanoic acid

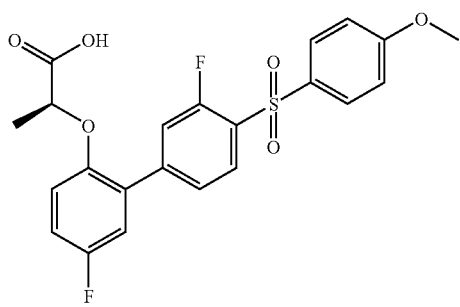

i) 4-bromo-2-fluoro-1-[(4-methoxyphenyl)sulfonyl]benzene

The subtitle compound was prepared by the method of example 9 step (i) using 4-bromo-2-fluorobenzenesulfonyl chloride and anisole.
¹H NMR DMSO-d6: δ 7.94 (1H, t), 7.89-7.85 (2H, m), 7.8 (1H, dd), 7.71-7.68 (1H, m), 7.18-7.14 (2H, m), 3.84 (3H, s).

ii) 2-(benzyloxy)-3',5-difluoro-4'-[(4-methoxyphenyl)sulfonyl]biphenyl

The subtitle compound was prepared by the method of example 2 step (ii) using the product of step (iii) and [2-(benzyloxy)-5-fluorophenyl]boronic acid.

¹H NMR DMSO-d6: δ 8.01 (1H, t), 7.9 (2H, d), 7.64 (1H, dd), 7.58 (1H, dd), 7.33-7.29 (6H, m), 7.26-7.23 (2H, m), 7.2-7.16 (2H, m), 5.12 (2H, s), 3.85 (3H, s).

iii) 3',5-difluoro-4'-[(4-methoxyphenyl)sulfonyl]biphenyl-2-ol

A suspension of the product of step (ii) (838 mg) in acetic acid (30 ml) and 10% Pd/C (200 mg) was stirred under 2 bar pressure of hydrogen for 30 min. The catalyst was removed by filtration and the filtrate was evaporated to give the subtitle compound, yield 630 mg.
¹H NMR DMSO-d6: δ 8.04-7.99 (1H, m), 7.91 (2H, dd), 7.68 (1H, dd), 7.6 (1H, dd), 7.23 (1H, dd), 7.18 (2H, dd), 7.09 (1H, td), 6.95 (1H, dd), 3.85 (3H, s).

iv) tert-butyl (2S)-2-({3',5-difluoro-4'-[(4-methoxyphenyl)sulfonyl]biphenyl-2-yl}oxy)propanoate The subtitle compound was prepared by the method of example 3 step (i) using the product of step (iii).
¹H NMR DMSO-d6: δ 8.08-8.02 (1H, m), 7.93 (2H, dd), 7.73 (1H, dd), 7.68 (1H, dd), 7.33 (1H, dd), 7.28-7.15 (3H, m), 7.02 (1H, dd), 4.91 (1H, q), 3.86 (3H, s), 1.41 (3H, d), 1.34 (9H, s).

v) (2S)-2-({3',5-difluoro-4'-[(4-methoxyphenyl)sulfonyl]biphenyl-2-yl}oxy)propanoic acid The title compound was prepared by the method of example 1 step (iv) using the product of step (iv).
¹H NMR DMSO-d6: δ 8.01 (1H, t), 7.92 (2H, d), 7.86 (1H, d), 7.78 (1H, dd), 7.26 (1H, dd), 7.20-7.12 (3H, m), 6.96 (1H, dd), 4.74 (1H, q), 3.85 (3H, s), 1.34 (3H, d).
MS: APCI(−ve) 447 (M−1)

EXAMPLE 13

(2S)-2-({3',5-difluoro-4'-[(3-fluorophenyl)sulfonyl]biphenyl-2-yl}oxy)propanoic acid

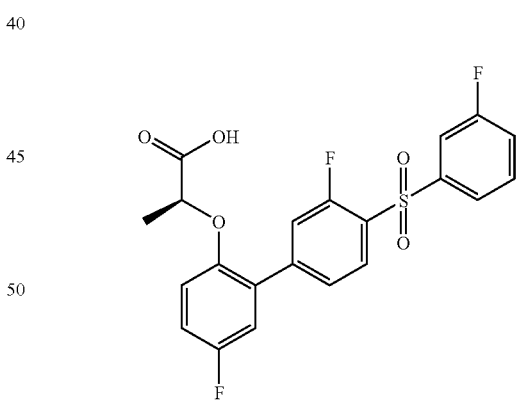

i) 1,1'-dithiobis(3-fluorobenzene)

The subtitle compound was prepared by the method of example 11 step (i) using 3-fluorobenzenethiol.
¹H NMR CDCl₃: δ 7.3-7.21 (6H, m), 6.92 (2H, tt).

ii) 4-bromo-2-fluoro-1-[(3-fluorophenyl)sulfonyl]benzene

A solution of the product of step (i) (1.98 g) and isoamyl nitrite (1.6 ml) in dry acetonitrile (25 ml) was stirred at 50° C.

4-bromo-2-fluoroaniline (1.23 g) was added portionwise and the reaction mixture was stirred at 60° C. for 2 h and then concentrated under reduced pressure. The residue (2.1 g) was dissolved in DCM (25 ml) and MCPBA (6 g) was added portionwise at 0° C. The reaction was stirred overnight at room temperature. The reaction was washed with aqueous sodium metabisulfite solution, aqueous NaHCO$_3$, dried (MgSO$_4$) and evaporated under reduced pressure. The residue was purified by chromatography on silica eluting with 9:1 isohexane/ethyl acetate to give the sub-title compound as a white solid (0.67 g).

$^1$H NMR CDCl$_3$: δ 7.96 (1H, td), 7.8 (1H, dq), 7.7 (1H, dq), 7.56-7.49 (2H, m), 7.33 (2H, dd).

iii) 3,5'-difluoro-2'-methoxybiphenyl-4-yl3-fluorophenyl sulfone

The subtitle compound was prepared by the method of example 2 step (ii) using the product of step (ii) and 5-fluoro-2-methoxybenzene boronic acid.

$^1$H NMR CDCl$_3$: δ 8.10 (1H, t), 7.85 (1H, d), 7.75 (1H, d), 7.54 (1H, td), 7.46 (1H, dd), 7.36-7.3 (2H, m), 7.07 (1H, ddd), 7.01 (1H, dd), 6.92 (1H, dd), 3.79 (3H, m).

iv) 3',5-difluoro-4'-[(3-fluorophenyl)sulfonyl]biphenyl-2-ol

The subtitle compound was prepared by the method of example 2 step (iii) using the product of step (iii).

MS: APCI(−ve) 363 (M−H)

v) methyl (2S)-2-({3',5-difluoro-4'-[(3-fluorophenyl)sulfonyl]biphenyl-2-yl}oxy)propanoate The subtitle compound was prepared by the method of example 11 step (vii) using the product of step (iv) and the product of example 11 step (vi).

$^1$H NMR CDCl$_3$: δ 8.11 (1H, t), 7.86 (2H, d), 7.76 (1H, d), 7.58-7.51 (2H, m), 7.47 (1H, dd), 7.33 (1H, dd), 7.04-6.98 (2H, m), 6.82-6.77 (1H, m), 4.72 (1H, q), 3.72 (3H, s), 1.51 (3H, d).

vi) (2S)-2-({3',5-difluoro-4'-[(3-fluorophenyl)sulfonyl]biphenyl-2-yl}oxy)propanoic acid The title compound was prepared by the method of example 11 step (viii) using the product of step (v).

$^1$H NMR DMSO-d6: δ 8.1 (1H, t), 7.87-7.736 (5H, m), 7.67 (1H, td), 7.33 (1H, dd), 7.24 (1H, td), 7.03 (1H, dd), 4.96 (1H, q), 1.43 (3H, d).

MS: APCI(−ve) 435 (M−H)

EXAMPLE 14

({5-chloro-4'-[(4-fluorophenyl)sulfonyl]-2'-methylbiphenyl-2-yl}oxy)acetic acid

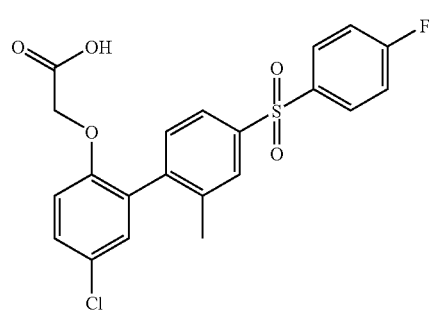

i) 4-bromo-3-methylphenyl 4-fluorophenyl sulfone

The subtitle compound was prepared by the method of example 9 step (i) using 4-bromo-3-methylbenzene sulfonyl chloride and fluorobenzene.

$^1$H NMR CDCl$_3$: δ 7.97-7.92 (2H, m), 7.77 (1H, d), 7.67 (1H, d), 7.59 (1H, dd), 7.19 (2H, t), 2.45 (3H, s).

ii) 5'-chloro-4-[(4-fluorophenyl)sulfonyl]-2'-methoxy-2-methylbiphenyl

The subtitle compound was prepared by the method of example 2 step (ii) using the product of step i) and 5-chloro-2-methoxybenzene boronic acid.

MS: APCI(+ve) 391 (M+H)$^-$ iii) 5-chloro-4'-[(4-fluorophenyl)sulfonyl]-2'-methylbiphenyl-2-ol

The subtitle compound was prepared by the method of example 2 step (iii) using the product of step (ii).

MS: APCI(−ve) 375 (M−H)

iv) tert-butyl ({5-chloro-4'-[(4-fluorophenyl)sulfonyl]-2'-methylbiphenyl-2-yl}oxy)acetate The subtitle compound was prepared by the method of example 1 step (iii) using the product from step (iii).

MS: APCI(+ve) 435 (M−tBu)

v) ({5-chloro-4'-[(4-fluorophenyl)sulfonyl]-2'-methylbiphenyl-2-yl}oxy)acetic acid The title compound was prepared by the method of example 1 step (iv) using the product from step (iv).

$^1$H NMR DMSO-d6: δ 8.10 (2H, ddd), 7.89 (1H, d), 7.8 (1H, dd), 7.49 (2H, tt), 7.43-7.39 (2H, m), 7.20 (1H, d), 6.99 (1H, d), 4.66 (2H, s), 2.2 (3H, s).

MS: APCI−ve 447 (M−1)

EXAMPLE 15

(2S)-2-{[2'-chloro-5-fluoro-4'-(phenylsulfonyl)biphenyl-2-yl]oxy}propanoic acid

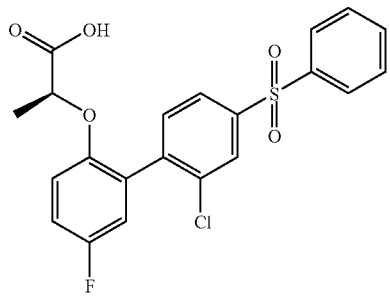

i) 4-bromo-3-chlorophenyl phenyl sulfone

The subtitle compound was prepared by the method of example 9 step (i) using 4-bromo-3-chlorobenzenesulfonyl chloride and benzene.
$^1$H NMR DMSO-d6: δ 8.19 (1H, d), 8.05-8.03 (3H, m), 7.83 (1H, dd), 7.74 (1H, t), 7.65 (2H, t).

ii) 2-chloro-5'-fluoro-2'-methoxybiphenyl-4-yl phenyl sulfone

The subtitle compound was prepared by the method of example 2 step (ii) using the product of step (i) and 5-fluoro-2-methoxybenzene boronic acid.
$^1$H NMR DMSO-d6: δ 8.11-8.07 (3H, m), 7.96 (1H, dd), 7.78-7.73 (1H, m), 7.68 (2H, t), 7.59 (1H, d), 7.28 (1H, td), 7.16-7.11 (2H, m), 3.69 (3H, s).

iii) 2'-chloro-5-fluoro-4'-(phenylsulfonyl)biphenyl-2-ol

The subtitle compound was prepared by the method of example 2 step (iii) using the product of step (ii).
$^1$H NMR DMSO-d6: δ 9.68 (1H, s), 8.09-8.06 (3H, m), 7.94 (1H, dd), 7.77-7.72 (1H, m), 7.7-7.65 (2H, m), 7.59 (1H, d), 7.10 (1H, td), 7.02 (1H, dd), 6.92 (1H, dd).

iv) tert-butyl (2S)-2-{[2'-chloro-5-fluoro-4'-(phenylsulfonyl)biphenyl-2-yl]oxy}propanoate The subtitle compound was prepared by the method of example 3 step (i) using the product of step (iii).
$^1$H NMR DMSO-d6: δ 8.12-8.06 (3H, m), 8.019-7.95 (1H, m), 7.79-7.72 (1H, m), 7.67 (3H, t), 7.25 (1H, td), 7.17 (1H, dd), 6.95 (1H, dd), 4.77-4.68 (1H, m), 1.32 (9H, s), 1.26 (3H, d).

v) (2S)-2-{[2'-chloro-5-fluoro-4'-(phenylsulfonyl)biphenyl-2-yl]oxy}propanoic acid The subtitle compound was prepared by the method of example 3 step (i) using the product of step (iii).
$^1$H NMR DMSO-d6: δ 8.12-8.07 (3H, m), 7.97 (1H, dd), 7.8-7.65 (4H, m), 7.21 (1H, td), 7.14 (1H, dd), 6.96 (1H, dd), 4.69-4.6 (1H, m), 1.25 (3H, d).
MS: APCI−ve 433 (M−1)

EXAMPLE 16

({3'-fluoro-4'-[(4-fluorophenyl)sulfonyl]-5-methylbiphenyl-2-yl}oxy)acetic acid

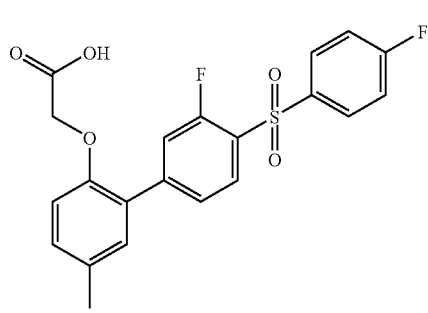

i) 3-fluoro-2'-methoxy-5'-methylbiphenyl-4-yl 4-fluorophenyl sulfone

The subtitle compound was prepared by the method of example 2 step (ii) using the product of example 4 step (i) and (2-methoxy-5-methylphenyl)boronic acid.
$^1$H NMR DMSO-d6: δ 8.10-8.03 (3H, m), 7.60 (1H, dd), 7.55-7.50 (3H, m), 7.23 (1H, dd), 7.20 (1H, d), 7.04 (1H, d), 3.74 (3H, s), 2.28 (3H, s).

ii) 3'-fluoro-4'-[(4-fluorophenyl)sulfonyl]-5-methylbiphenyl-2-ol

The subtitle compound was prepared by the method of example 2 step (iii) using the product of step (i).
$^1$H NMR DMSO-d6: δ 9.71 (1H, s), 8.09-8.02 (3H, m), 7.68 (1H, dd), 7.59 (1H, dd), 7.54-7.49 (2H, m), 7.16 (1H, d), 7.05 (1H, dd), 6.86 (1H, d), 2.23 (3H, s).

iii) tert-butyl ({3'-fluoro-4'-[(4-fluorophenyl)sulfonyl]-5-methylbiphenyl-2-yl}oxy)acetate The subtitle compound was prepared by the method of example 1 step (iii) using the product of step (ii).
$^1$H NMR DMSO-d6: δ 8.09-8.04 (3H, m), 7.69-7.63 (2H, m), 7.55-7.49 (2H, m), 7.24 (1H, d), 7.19 (1H, dd), 6.93 (1H, d), 4.67 (2H, s), 2.28 (3H, s), 1.38 (9H, s).

iv) ({3'-fluoro-4'-[(4-fluorophenyl)sulfonyl]-5-methylbiphenyl-2-yl}oxy)acetic acid The subtitle compound was prepared by the method of example 1 step (iv) using the product of step (iii).
$^1$H NMR DMSO-d6: δ 8.1-8.03 (3H, m), 7.71-7.67 (2H, m), 7.55-7.49 (2H, m), 7.23 (1H, d), 7.19 (1H, dd), 6.95 (1H, d), 4.71 (2H, s), 2.27 (3H, s).
MS: APCI−ve 417 (M−1).

EXAMPLE 17

({5-chloro-4'-[(4-methoxyphenyl)sulfonyl]biphenyl-2-yl}oxy)acetic acid

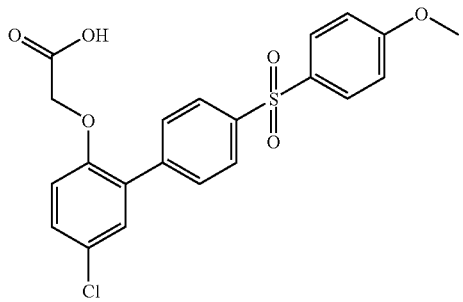

1-bromo-4-[(4-methoxyphenyl)sulfonyl]benzene

The subtitle compound was prepared by the method of example 9 step (i) using 4-bromobenzenesulfonyl chloride and anisole.

$^1$H NMR DMSO-d6: δ 7.91-7.87 (2H, m), 7.86-7.80 (4H, m), 7.16-7.12 (2H, m), 3.83 (3H, s).

ii) 2-(benzyloxy)-3',5-difluoro-4'-[(4-methoxyphenyl)sulfonyl]biphenol

The subtitle compound was prepared by the method of example 2 step (ii) using the product of step (i) and [2-(benzyloxy)-5-chlorophenyl]boronic acid.

$^1$H NMR DMSO-d6: δ 7.95-7.91 (4H, m), 7.77-7.74 (2H, m), 7.43 (1H, dd), 7.40 (1H, d), 7.31-7.29 (5H, m), 7.23 (1H, d), 7.16-7.13 (2H, m), 5.14 (2H, s), 3.83 (3H, s).

iii) 3',5-difluoro-4'-[(4-methoxyphenyl)sulfonyl]biphenyl-2-ol

The subtitle compound was prepared by the method of example 12 step (iii) using the product of step (ii) and 10% Pd/C in acetic acid.

1H NMR DMSO-d6: δ 7.95-7.89 (4H, m), 7.76 (2H, dd), 7.32 (1H, d), 7.25 (1H, dd), 7.16-7.11 (2H, m), 6.97 (1H, d), 3.83 (3H, d).

iv) tert-butyl ({5-chloro-4'-[(4-methoxyphenyl)sulfonyl]biphenyl-2-yl}oxy)acetate The subtitle compound was prepared by the method of example 1 step (iii) using the product of step (iii) and tert-butyl bromoacetate which was used directly in step (v) without further characterisation.

v) ({5-chloro-4'-[(4-methoxyphenyl)sulfonyl]biphenyl-2-yl}oxy)acetic acid

The subtitle compound was prepared by the method of example 1 step (iv) using the product of step (iv).

$^1$H NMR DMSO-d6: δ 7.96-7.91 (4H, m), 7.81-7.78 (2H, m), 7.42-7.39 (2H, m), 7.15 (2H, dd), 7.06 (1H, dd), 4.74 (2H, s), 3.83 (3H, s).

EXAMPLE 18

({4'-[(2-chlorophenyl)sulfonyl]-3',5-difluorobiphenyl-2-yl}oxy)acetic acid

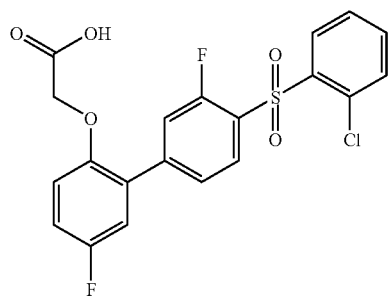

i) 1,1'-dithiobis(2-chlorobenzene)

Hexamethyldisilazane (4.4 ml) was added to a stirred solution of 2-chlorobenzenethiol (2.0 ml) and DMSO (3.7 ml) in dry acetonitrile at room temperature. After 2 h the white precipitate was filtered and washed (cold acetonitrile) to give the sub-title compound as a white solid (2.27 g).

$^1$H NMR CDCl$_3$: δ 7.56 (2H, dd), 7.36 (2H, dd), 7.26-7.14 (4H, m).

ii) 4-bromo-1-[(2-chlorophenyl)sulfonyl]-2-fluorobenzene

The subtitle compound was prepared by the method of example 13 step (ii) using the product of step (i) and 4-bromo-2-fluoroaniline.

$^1$H NMR CDCl$_3$: δ 8.38 (1H, dt), 8.10 (1H, dd), 7.60-7.51 (3H, m), 7.45 (1H, dd), 7.29 (1H, dd).

iii) 2-chlorophenyl 3,5'-difluoro-2'-methoxybiphenyl-4-yl sulfone

The subtitle compound was prepared by the method of example 2 step (ii) using the product of step (ii) and 5-fluoro-2-methoxybenzene boronic acid which was used directly in step (iv) without further characterisation.

iv) 4'-[(2-chlorophenyl)sulfonyl]-3',5-difluorobiphenyl-2-ol

The subtitle compound was prepared by the method of example 2 step (iii) using the product of step (iii) and boron tribromide.

MS: MM(−ve) 379 (M−H)

v) tert-butyl ({4'-[(2-chlorophenyl)sulfonyl]-3',5-difluorobiphenyl-2-yl}oxy)acetate The sub-title compound was prepared by the method of example 1 step (iii) using the product of step (iv) which was used directly in step (iv) without further characterisation.

vi) ({4'-[(2-chlorophenyl)sulfonyl]-3',5-difluorobiphenyl-2-yl}oxy)acetic acid

The title compound was prepared by the method of example 1 step (iv) using the product of step (v).
¹H NMR DMSO-d6: δ 8.32 (1H, d), 8.14 (1H, t), 7.82-7.67 (5H, m), 7.36 (1H, dd), 7.24 (1H, td), 7.09 (1H, dd), 4.74 (2H, s).
MS: MM(-ve) 437 (M-H).

EXAMPLE 19

(2S)-2-{[3'-chloro-5-fluoro-4'-(phenylsulfonyl)biphenyl-2-yl]oxy}propanoic acid

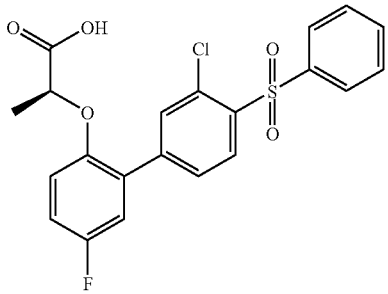

i) 4-bromo-2-chloro-1-(phenylsulfonyl)benzene

The sub-title compound was prepared by the method of example 9 step (i) using 4-bromo-2-chlorobenzenesulfonyl chloride and benzene.
MS: MM(-ve) 331 (M-H).

ii) 3'-chloro-5-fluoro-2-methoxy-4'-(phenylsulfonyl) biphenyl

The subtitle compound was prepared by the method of example 2 step (ii) using the product of step (i) and 5-fluoro-2-methoxybenzene boronic acid.
¹H NMR DMSO-d6: δ 8.37 (1H, dd), 8.00 (2H, dd), 7.61 (3H, dd), 7.53 (2H, td), 7.07 (1H, ddd), 7.02 (1H, dd), 6.92 (1H, dd), 3.79 (3H, s).

iii) 3'-chloro-5-fluoro-4'-(phenylsulfonyl)biphenyl-2-ol

The subtitle compound was prepared by the method of example 2 step (iii) using the product of step (ii).
MS: MM(-ve) 361 (M-H).

iv) methyl (2S)-2-{[3'-chloro-5-fluoro-4'-(phenylsulfonyl)biphenyl-2-yl]oxy}propanoate The subtitle compound was prepared by the method of example 11 step (vii) using the product of step (iii) and the product of example 11 step (vi).
MS: MM(+ve) 449 (M+H).

v) (2S)-2-{[3'-chloro-5-fluoro-4'-(phenylsulfonyl) biphenyl-2-yl]oxy}propanoic acid The title compound was prepared by the method of example 11 step (viii) using the product of step (iv).
¹H NMR DMSO-d6: δ 8.32 (1H, d), 7.98-7.96 (3H, m), 7.93 (1H, dd), 7.76 (1H, tt), 7.67 (2H, t), 7.35 (1H, dd), 7.23 (1H, td), 7.03 (1H, dd), 4.95 (1H, q), 1.42 (3H, d).
MS: MM(-ve) 433 (M-H).

EXAMPLE 20

({4'-[(3-chlorophenyl)sulfonyl]-2',5-difluorobiphenyl-2-yl}oxy)acetic acid

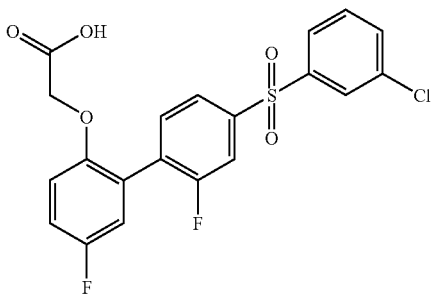

i) 1,1'-dithiobis(3-chlorobenzene)

The subtitle compound was prepared by the method of example 11 step (i) using 3-chlorobenzenethiol.
MS: MM(+ve) 287 (M+H).

ii) 1-bromo-4-[(3-chlorophenyl)sulfonyl]-2-fluorobenzene

The subtitle compound was prepared by the method of example 13 step (ii) using the product of step (i) and 4-bromo-3-fluoroaniline.
¹H NMR CDCl₃: δ 7.91 (1H, t), 7.82 (1H, dt), 7.74 (1H, dd), 7.68 (1H, dd), 7.61 (1H, dd), 7.59-7.56 (1H, m), 7.48 (1H, t).

iii) 3-chlorophenyl 2,5'-difluoro-2'-methoxybiphenyl-4-yl sulfone

The subtitle compound was prepared by the method of example 2 step (ii) using the product of step (ii) and 5-fluoro-2-methoxybenzene boronic acid.
MS: APCI(-ve) 393 (M-H).

iv) 4'-[(3-chlorophenyl)sulfonyl]-2',5-difluorobiphenyl-2-ol

The subtitle compound was prepared by the method of example 2 step (iii) using the product of step (iii) and boron tribromide.
MS: APCI(-ve) 381 (M-H)

v) tert-butyl ({4'-[(3-chlorophenyl)sulfonyl]-2',5-difluorobiphenyl-2-yl}oxy)acetate The sub-title compound was prepared by the method of example 1 step (iii) using the product of step (iv).
¹H NMR DMSO-d6: δ 8.10 (1H, t), 7.98 (2H, dd), 7.55-7.49 (3H, m), 7.45 (1H, dd), 7.07-7.02 (2H, m), 6.80 (1H, dd), 4.48 (2H, s), 1.44 (9H, s).

vi) ({4'-[(3-chlorophenyl)sulfonyl]-2',5-difluorobiphenyl-2-yl}oxy)acetic acid

The title compound was prepared by the method of example 1 step (iv) using the product of step (v).

$^1$H NMR DMSO-d6: δ 8.09 (1H, t), 8.00 (2H, t), 7.77-7.72 (4H, m), 7.32 (1H, dd), 7.24 (1H, td), 7.09 (1H, dd), 4.74 (2H, s).

MS: MM(−ve) 437 (M−H).

EXAMPLE 21

({2'-fluoro-4'-[(4-fluorophenyl)sulfonyl]-5-methylbiphenyl-2-yl}oxy)acetic acid

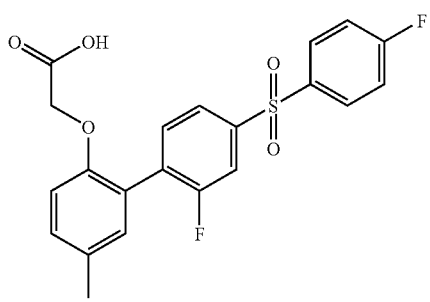

i) 2-fluoro-2'-methoxy-5'-methylbiphenyl-4-yl 4-fluorophenyl sulfone

The subtitle compound was prepared by the method of example 2 step (ii) using the product of example 9 step (i) and 5-methyl-2-methoxybenzene boronic acid.

$^1$H NMR DMSO-d6: δ 8.00 (2H, ddd), 7.73 (1H, dd), 7.66 (1H, dd), 7.49 (1H, dd), 7.24-7.18 (3H, m), 7.01 (1H, d), 6.89 (1H, d), 3.76 (3H, s), 2.31 (3H, s).

ii) 2'-fluoro-4'-[(4-fluorophenyl)sulfonyl]-5-methylbiphenyl-2-ol

The subtitle compound was prepared by the method of example 2 step (iii) using the product of step (i).

MS: MM(−ve) 360 (M−H)

iii) tert-butyl ({2'-fluoro-4'-[(4-fluorophenyl)sulfonyl]-5-methylbiphenyl-2-yl}oxy)acetate The subtitle compound was prepared by the method of example 1 step (iii) using the product of step (ii).

MS: MM(−ve) 472 (M−H).

v) ({2'-fluoro-4'-[(4-fluorophenyl)sulfonyl]-5-methylbiphenyl-2-yl}oxy acetic acid The title compound was prepared by the method of example 1 step (iv) using the product of step (iii).

$^1$H NMR DMSO-d6: δ 8.14 (2H, ddd), 7.90 (1H, dd), 7.84 (1H, dd), 7.68 (1H, t), 7.50 (2H, dd), 7.20 (1H, dd), 7.09 (1H, s), 6.90 (1H, d), 4.62 (2H, s), 2.22 (3H, s).

MS: MM(−ve) 417 (M−H).

EXAMPLE 22

{[3'-fluoro-5-methyl-4'-(phenylsulfonyl)biphenyl-2-yl]oxy}acetic acid

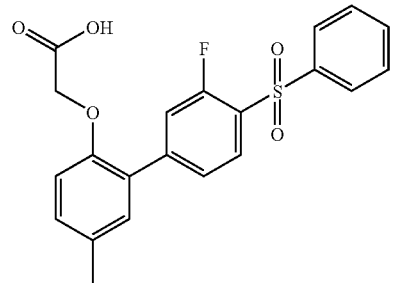

i) 3'-fluoro-2-methoxy-5-methyl-4'-(phenylsulfonyl)biphenyl

The subtitle compound was prepared by the method of example 2 step (ii) using the product of example 2 step (i) and (2-methoxy-5-methylphenyl)boronic acid.

MS: ES+ve 357 (M+1).

ii) 3'-fluoro-5-methyl-4'-(phenylsulfonyl)biphenyl-2-ol

The subtitle compound was prepared by the method of example 2 step (iii) using the product of step (i).

MS: APCI−ve 341 (M−1).

iii) tert-butyl {[3'-fluoro-5-methyl-4'-(phenylsulfonyl)biphenyl-2-yl]oxy}acetate The subtitle compound was prepared by the method of example 1 step (iii) using the product of step (ii).

MS: APCI−ve 401 (M−[t-butyl]).

iv) {[3'-fluoro-5-methyl-4'-(phenylsulfonyl)biphenyl-2-yl]oxy}acetic acid

The subtitle compound was prepared by the method of example 1 step (iv) using the product of step (iii).

$^1$H NMR DMSO-d6: δ 8.06 (1H, t), 7.99 (2H, d), 7.77 (1H, tt), 7.70-7.66 (4H, m), 7.23 (1H, d), 7.18 (1H, dd), 6.94 (1H, d), 4.71 (2H, s), 2.27 (3H, s).

MS: APCI−ve 399 (M−1).

EXAMPLE 23

{[5-chloro-3',5'-difluoro-4'-(phenylsulfonyl)biphenyl-2-yl]oxy}acetic acid

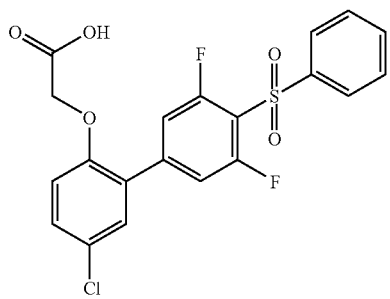

i) 4-bromo-2,6-difluorophenyl phenyl sulfone

A solution of diphenyl disulphide (1.26 g) and isoamyl nitrite (1.2 ml) in dry acetonitrile (20 ml) was stirred at 50° C. 4-bromo-2,6-difluoroaniline (1.0 g) was added portionwise and the reaction mixture was stirred at 60° C. for 2 h and then concentrated under reduced pressure. The residue (2.1 g) was dissolved in acetic acid (7.5 ml) and hydrogen peroxide (0.7 ml, 30% in aqueous w/w) was added and the mixture stirred overnight at 100° C. Ice was added, the mixture stirred for a further 30 mins and the beige solid filtered off (0.76 g) and taken through to the next step without further purification.

ii) 5'-chloro-3,5-difluoro-2'-methoxybiphenyl-4-yl phenyl sulfone

The subtitle compound was prepared by the method of example 2 step (ii) using the product of step (i) and 5-chloro-2-methoxybenzene boronic acid which was used directly in step (iv) without further characterisation.
MS: MM(−ve) 394 (M−H).

iii) 4'-[(2-chlorophenyl)sulfonyl]-3',5-difluorobiphenyl-2-ol

The subtitle compound was prepared by the method of example 2 step (iii) using the product of step (ii) and boron tribromide.
MS: MM(−ve) 379 (M−H).

iv) tert-butyl {[5-chloro-3',5'-difluoro-4'-(phenylsulfonyl)biphenyl-2-yl]oxy}acetate The sub-title compound was prepared by the method of example 1 step (iii) using the product of step (iii) which was used directly in step (iv) without further purification.
MS: ES(+ve) 495 (M+H).

v) {[5-chloro-3',5'-difluoro-4'-(phenylsulfonyl)biphenyl-2-yl]oxy}acetic acid The title compound was prepared by the method of example 1 step (iv) using the product of step (v).
$^1$H NMR DMSO-d6: δ 8.04 (2H, d), 7.81 (1H, tt), 7.71 (2H, t), 7.65 (1H, s), 7.62 (1H, s), 7.54 (1H, d), 7.46 (1H, dd), 7.12 (1H, d), 4.80 (2H, s).
MS: MM(−ve) 437 (M−H).

Rat Pharmacokinetic Data
IV and PO Rat Pharmacokinetic Studies

Test samples are made up at 1 mg/ml in an appropriate solvent and administered to Sprague Dawley rats either via the tail vein (IV, 1 ml/kg) or via the mouth (PO, 3 ml/cg). Blood samples are removed from the tail vein (reverse side to IV administration) at a series of time points and placed on ice. Blood samples are centrifuged and the plasma removed for analysis. Plasma samples are then analysed using MS/MS and concentrations of parent compound determined from a standard curve. The plasma concentration-time plot is analysed using the commercial software WinNonLin 3.1 (Pharsight, Mountain View, Calif.). Pharmacokinetic parameters such as clearance, volume of distribution and half-life are determined. Compounds of formula (I) have a half life>2.5 hours.

Pharmacological Data
Ligand Binding Assay

[$^3$H]PGD$_2$ was purchased from Perkin Elmer Life Sciences with a specific activity of 100-210 Ci/mmol. All other chemicals were of analytical grade.

HEK cells expressing rhCRTh2/Gα16 were routinely maintained in DMEM containing 10% Foetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 0.1 mM dithiothreitol, 1 mM EDTA, 0.1 mM phenyl methyl sulphonyl fluoride and 100 μg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C. The final pellet was re-suspended in 4 ml of membrane homogenisation buffer per cell factory used and the protein content determined. Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 μg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 μl of 6.25 nM [$^3$H]PGD$_2$, 20 μl membrane saturated SPA beads both in assay buffer and 10 μl of compound solution or 13,14-dihydro-15-keto prostaglandin D$_2$ (DK-PGD$_2$, for determination of non-specific binding, Cayman chemical company). Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at room temperature for 2 hours and counted on a Wallac Microbeta liquid scintillation counter (1 minute per well). Compounds of formula (I) have a $pIC_{50}$ value of >8.5.

Specifically example 7 has a $pIC_{50}$ value of 8.5; example 8 has a $pIC_{50}$ value of 8.8; example 15 has a $pIC_{50}$ value of 8.8.

The invention claimed is:

1. A compound having the following formula or a pharmaceutically acceptable salt thereof:

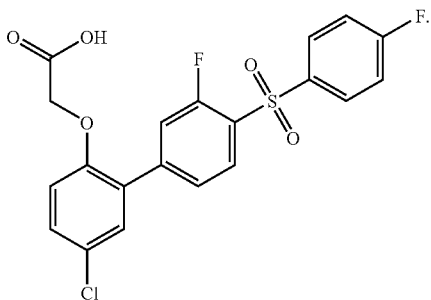

2. The compound or salt of claim 1, wherein the pharmaceutically acceptable salt is a sodium, potassium, calcium, aluminium, lithium, magnesium, zinc, benzathine, chloroprocaine, choline, diethanolamine, ethanolamine, ethyldiamine, tertiarybutylamine, meglumine, tromethamine or procaine salt.

3. The compound or salt of claim 1, wherein the pharmaceutically acceptable salt is a hydrochloride, hydrobromide, phosphate, acetate, fumarate, maleate, tartrate, citrate, oxalate, methanesulphonate or p-toluenesulphonate salt.

4. A pharmaceutical composition comprising a compound or salt as claimed in any one of claims 1, 2, or 3 in association with a pharmaceutically acceptable carrier.

5. A method for the therapeutic treatment of asthma in a patient suffering from asthma, which comprises administering to the patient a therapeutically effective amount of a compound or salt as claimed in any one of claims 1, 2, or 3.

6. A method for the therapeutic treatment of rhinitis in a patient suffering from rhinitis, which comprises administering to the patient a therapeutically effective amount of a compound or salt as claimed in any one of claims 1, 2, or 3.

7. A method for the therapeutic treatment of COPD in a patient suffering from COPD, which comprises administering to the patient a therapeutically effective amount of a compound or salt as claimed in any one of claims 1, 2, or 3.

* * * * *